(12) United States Patent
Sato et al.

(10) Patent No.: US 10,367,231 B2
(45) Date of Patent: Jul. 30, 2019

(54) MAGNESIUM-CONTAINING ELECTROLYTIC SOLUTION

(71) Applicant: FUJIFILM Wako Pure Chemical Corporation, Osaka-shi, Osaka (JP)

(72) Inventors: Kazuhiko Sato, Kawagoe (JP); Takahiro Kiyosu, Kawagoe (JP); Hironori Mizuta, Kawagoe (JP); Goro Mori, Kawagoe (JP); Kuniaki Okamoto, Kawagoe (JP)

(73) Assignee: FUJIFILM Wako Pure Chemical Corporation, Osaka (JP)

( * ) Notice: Subject to any disclaimer, the term of this patent is extended or adjusted under 35 U.S.C. 154(b) by 0 days.

(21) Appl. No.: 15/529,902

(22) PCT Filed: Nov. 27, 2015

(86) PCT No.: PCT/JP2015/083325
§ 371 (c)(1),
(2) Date: May 25, 2017

(87) PCT Pub. No.: WO2016/084924
PCT Pub. Date: Jun. 2, 2016

(65) Prior Publication Data
US 2017/0331154 A1 Nov. 16, 2017

(30) Foreign Application Priority Data

Nov. 28, 2014 (JP) .................. 2014-240753

(51) Int. Cl.
*H01M 4/38* (2006.01)
*H01M 10/0568* (2010.01)
(Continued)

(52) U.S. Cl.
CPC .......... *H01M 10/0568* (2013.01); *C07F 3/02* (2013.01); *C07F 5/064* (2013.01); *C07F 7/0836* (2013.01);
(Continued)

(58) Field of Classification Search
CPC ............. H01M 4/381; H01M 10/0568; H01M 10/054; H01M 10/0567; H01M 10/0569;
(Continued)

(56) References Cited

U.S. PATENT DOCUMENTS 4,727,172 A * 2/1988 Yamamoto ............ C07F 7/0838
556/440
2001/0027162 A1 10/2001 Hirahata et al.
(Continued)

FOREIGN PATENT DOCUMENTS

JP 2000026437 1/2000
JP 2004107641 4/2004
(Continued)

OTHER PUBLICATIONS

Machine translation of WO 2013/185562 (no date).*
(Continued)

*Primary Examiner* — Amanda C. Walke
(74) *Attorney, Agent, or Firm* — Hamre, Schumann, Mueller & Larson, P.C.

(57) ABSTRACT

It is an object of the present invention to provide an electrolytic solution having high oxidation decomposition potential, where dissolution and deposition of magnesium proceed repeatedly and stably, using a non-nucleophilic alkoxide-type magnesium salt.
The present invention relates to
(1) an electrolytic solution for a magnesium battery comprising a mixture of a compound represented by the following general formula (I), a Lewis acid and a solvent:
(Continued)

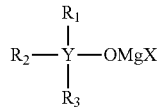

(2) an electrochemical device comprising the electrolytic solution, a positive electrode and a negative electrode, and
(3) a compound represented by the following general formula (I'):

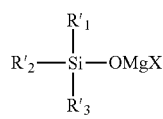

11 Claims, 2 Drawing Sheets

(51) Int. Cl.
| H01M 10/0569 | (2010.01) |
| C07F 5/06 | (2006.01) |
| H01M 10/056 | (2010.01) |
| H01M 10/36 | (2010.01) |
| C07F 3/02 | (2006.01) |
| H01M 10/054 | (2010.01) |
| C07F 19/00 | (2006.01) |
| C07F 7/08 | (2006.01) |
| H01M 10/0567 | (2010.01) |

(52) U.S. Cl.
CPC ........... *C07F 19/005* (2013.01); *H01M 4/381* (2013.01); *H01M 10/054* (2013.01); *H01M 10/056* (2013.01); *H01M 10/0569* (2013.01); *H01M 10/365* (2013.01); *H01M 10/0567* (2013.01); *H01M 2300/0025* (2013.01); *Y02E 60/13* (2013.01)

(58) Field of Classification Search
CPC . H01M 10/365; H01M 10/056; C07F 7/0836; C07F 5/064; C07F 3/02; C07F 19/005

USPC ........................................................ 429/199
See application file for complete search history.

(56) References Cited

U.S. PATENT DOCUMENTS

| 2004/0137324 | A1 | 7/2004 | Itaya et al. |
| 2005/0256256 | A1 | 11/2005 | Muramoto et al. |
| 2007/0048605 | A1 | 3/2007 | Pez et al. |
| 2009/0171045 | A1 | 7/2009 | Kumamoto |
| 2011/0111286 | A1 | 5/2011 | Yamamoto et al. |
| 2011/0171536 | A1 | 7/2011 | Oki et al. |
| 2012/0219867 | A1 | 8/2012 | Nuli et al. |
| 2015/0056499 | A1* | 2/2015 | Dai ................... H01M 10/0568 429/200 |
| 2015/0140451 | A1 | 5/2015 | Yang et al. |

FOREIGN PATENT DOCUMENTS

| JP | 2004213991 | 7/2004 |
| JP | 2004265676 | 9/2004 |
| JP | 2007087938 | 4/2007 |
| JP | 2007157416 | 6/2007 |
| JP | 2009173870 | 8/2009 |
| JP | 2010015979 | 1/2010 |
| JP | 2012182124 | 9/2012 |
| JP | 2014022365 | 2/2014 |
| WO | 2012160587 | 11/2012 |
| WO | 2013185562 | 12/2013 |

OTHER PUBLICATIONS

Aurback, D. et al., "Prototype systems for rechargeable magnesium batteries," letters to nature, Nature. vol. 407, Oct. 12, 2000, pp. 724-727.
Wang, Fei-fei et al., "A novel electrolyte system without a Grignard reagent for rechargeable magnesium batteries," Chemical Communications, The Royal Society of Chemistry. 2012, vol. 48, Issue 87, pp. 10763-10765.
Liao, Chen et al., "Highly soluble alkoxide magnesium salts for rechargeable magnesium batteries," The Royal Society of Chemistry, Journal of Materials Chemistry A. 2014, 2, pp. 581-584.
International Search Report for International Application Serial No. PCT/JP2015/083325, dated Mar. 1, 2016, English translation, 5 pages.

* cited by examiner

[Figure 1]
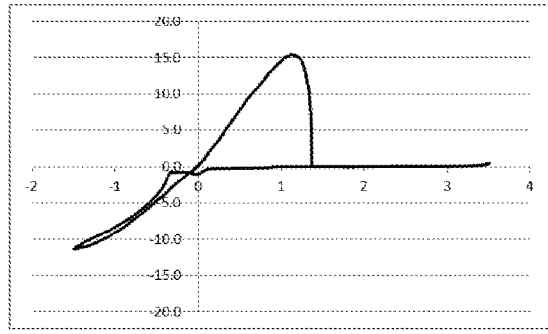
[Figure 2]
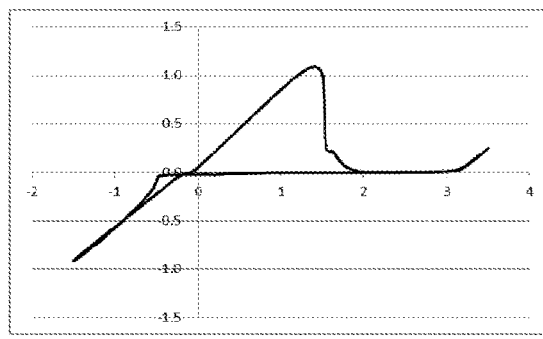
[Figure 3]
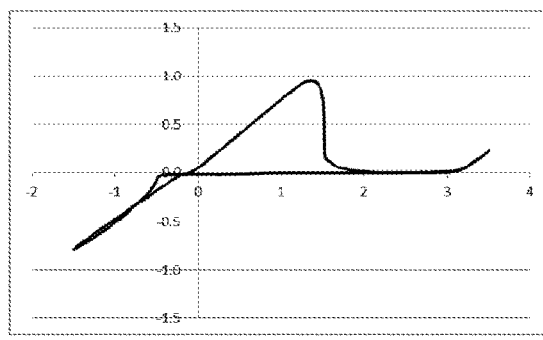
[Figure 4]
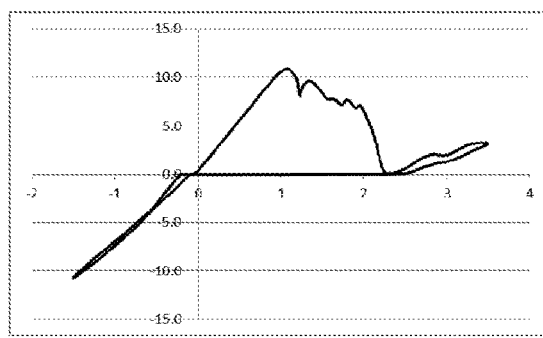

[Figure 5]
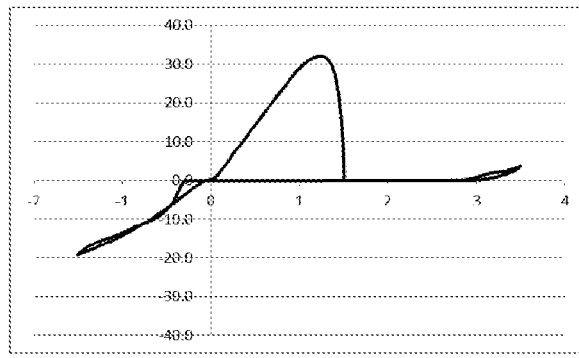
[Figure 6]
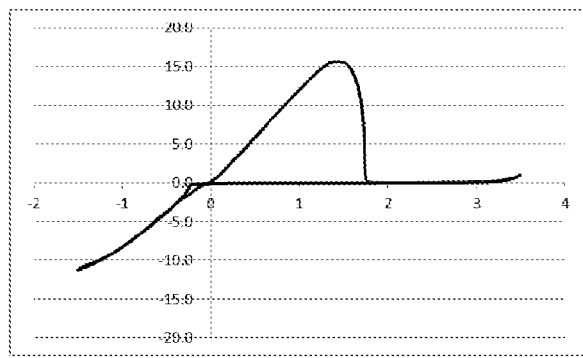
[Figure 7]
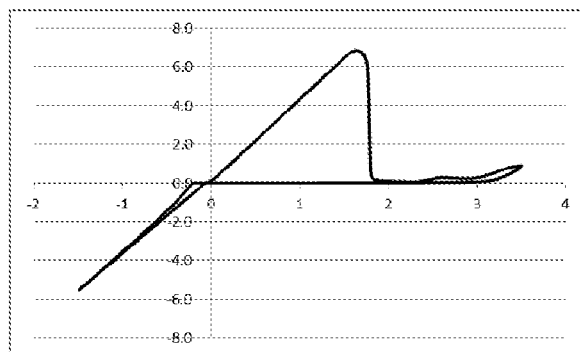

MAGNESIUM-CONTAINING ELECTROLYTIC SOLUTION

TECHNICAL FIELD

The present invention relates to a magnesium ion containing electrolytic solution and an electrochemical device comprising the electrolytic solution.

BACKGROUND ART

Magnesium has large electric capacity per unit volume, because an ion thereof is a polyvalent ion. In addition, magnesium has advantages of having not only higher melting point and safer, as compared with lithium, but also small deviation of resource distribution on the earth, and source amount is abundant and is thus cheap. Therefore, a magnesium ion battery adopting metal magnesium as a negative electrode has been noticed as the next generation battery, to replace a lithium ion battery.

However, in the magnesium ion battery adopting metal magnesium as a negative electrode, a passive film is formed on the electrode surface, by a reaction with an electrolytic solution, caused by high reducing performance of magnesium itself. Thus, it hinders reversible dissolution and deposition of magnesium, which makes a negative electrode reaction difficult.

As an electrolytic solution not forming such a passive film, there has been known an electrolytic solution, where a Grignard reagent, RMgX, (wherein R is an alkyl group or an aryl group and X is chlorine or bromine) is dissolved in tetrahydrofuran, where reversible dissolution and deposition of magnesium has been confirmed.

On the other hand, Aurbach et al. have reported that a THF solution of $Mg(AlCl_2BuEt)_2$ was prepared, using dibutyl magnesium, $Bu_2Mg$, and ethylaluminum dichloride, $EtAlCl_2$, and it can be used up to potential of about 2.4 V, relative to magnesium (NON-PATENT LITERATURE 1).

However, because these electrolytic solutions using the Grignard reagent or alkylmagnesium have nucleophilic property, there is concern of a direct reaction with an active material having high chemical activity or sulfur, which is used at the positive electrode, therefore, there has been limitation in use as a practical battery.

On the other hand, Wang et al. have reported an electrolytic solution which can be used up to about 2.6 V, relative to magnesium, by mixing a non-nucleophilic phenoxide-type magnesium salt and aluminum chloride (NON-PATENT LITERATURE 2).

In addition, Liao et al. have reported an oxidation resistant electrolytic solution of about 2.5 V, relative to magnesium, by mixing a non-nucleophilic alkoxide-type magnesium salt and aluminum chloride (NON-PATENT LITERATURE 3).

CITATION LIST

Non-Patent Literature

NON-PATENT LITERATURE 1: Nature, 407, p 724-727 (2000).

NON-PATENT LITERATURE 2: Chem. Commun., 2012, 48, 10763-10765.

NON-PATENT LITERATURE 3: J. Mater. Chem. A, 2014, 2, 581-584.

SUMMARY OF INVENTION

Technical Problem

The electrolytic solution described in NON-PATENT LITERATURE 2 or NON-PATENT LITERATURE 3 has been reported to have a wide potential window, using the non-nucleophilic magnesium salt as described above, however, the electrolytic solution operable in higher potential has been requested.

That is, it is an object of the present invention to provide the electrolytic solution having high oxidation decomposition potential, where dissolution and deposition of magnesium proceed repeatedly and stably, using a non-nucleophilic alkoxide-type magnesium salt.

Solution to Problem

The present invention relates to "an electrolytic solution for a magnesium battery comprising a mixture of a compound represented by the following general formula (I), a Lewis acid and a solvent:

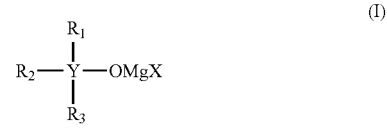

(wherein Y represents a carbon atom or a silicon atom, X represents a chlorine atom or a bromine atom, $R_1$ represents an aryl group having 6 to 10 carbon atoms, which may have a halogeno group, an alkyl group, a halogenoalkyl group or an alkoxy group, as a substituent, $R_2$ and $R_3$ each independently represent a magnesium chloride oxy group (—OMgCl); a magnesium bromide oxy group (—OMgBr); an alkenyl group having 1 to 6 carbon atoms; an alkyl group having 1 to 6 carbon atoms, which may have a halogeno group or an alkoxy group, as a substituent; or an aryl group having 6 to 10 carbon atoms, which may have a halogeno group, an alkyl group, a halogenoalkyl group, or an alkoxy group, as a substituent),"

"an electrochemical device comprising the electrolytic solution, a positive electrode and a negative electrode"; and "a compound represented by the following general formula (I'):

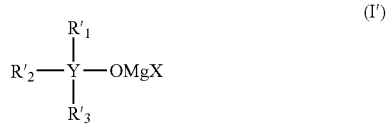

(wherein X represents a chlorine atom or a bromine atom, $R'_1$ represents an aryl group having 6 to 10 carbon atoms, which may have a halogeno group, an alkyl group, a halogenoalkyl group or an alkoxy group, as a substituent, $R'_2$ and $R'_3$ each independently represent a hydrogen atom; —OMgCl; —OMgBr; an alkenyl group having 1 to 6 carbon atoms; an alkyl group having 1 to 6 carbon atoms, which may have a halogeno group or an alkoxy group; or an aryl group having 6 to 10 carbon atoms, which may have a halogeno group, an alkyl group, a halogenoalkyl group or an alkoxy group, as a substituent.)".

Advantageous Effects of Invention

The electrolytic solution of the present invention can be used as an electrolytic solution of a high voltage magnesium battery, because of having high oxidation decomposition potential, as compared with a conventional electrolytic solution. In addition, the electrolytic solution of the present invention exerts such effect as dissolution and deposition of magnesium proceed repeatedly and stably, when used as an electrolytic solution for a magnesium secondary battery. Still more, the electrolytic solution of the present invention also has superior storage stability.

BRIEF EXPLANATION OF DRAWINGS

FIG. 1 represents a graph showing result after 10 cycles in CV measurement using an electrolytic solution 1, "a magnesium chloride triphenylmethoxide-aluminum chloride/tetrahydrofuran (THF) solution", in Example 7.

FIG. 2 represents a graph showing result after 10 cycles in CV measurement using an electrolytic solution 2, "a magnesium chloride triphenylmethoxide-aluminum chloride/triglyme solution", in Example 7.

FIG. 3 represents a graph showing result after 40 cycles in CV measurement using an electrolytic solution 2, "a magnesium chloride triphenylmethoxide-aluminum chloride/triglyme solution", in Example 7.

FIG. 4 represents a graph showing result after 10 cycles in CV measurement using a comparative electrolytic solution 1, "a (tert-BuOMgCl)$_6$—AlCl$_3$/THF solution", in Comparative Example 3.

FIG. 5 represents a graph showing result after 10 cycles in CV measurement using a comparative electrolytic solution 2, "a MgCl$_2$-Me$_2$AlCl—Bu$_4$NCl/THF solution", in Comparative Example 3.

FIG. 6 represents a graph showing result after 10 cycles in CV measurement using an electrolytic solution 7, "a magnesium chloride triphenylsiloxide-aluminum chloride/ THF solution", in Example 16.

FIG. 7 represents a graph showing result after 10 cycles in CV measurement using a comparative electrolytic solution 3, "a (Me$_3$SiOMgCl)$_6$—AlCl$_3$/THF solution", in Comparative Example 5.

DESCRIPTION OF EMBODIMENTS

[Compound Represented by the General Formula (I)]

Y of the compound represented by the general formula (I) represents a carbon atom or a silicon atom, and a silicon atom is preferable. The compound represented by the general formula (I), wherein Y is a silicon atom, exhibits still more superior storage stability, as compared with the case wherein Y is a carbon atom.

X of the compound represented by the general formula (I) represents a chlorine atom or a bromine atom, and a chlorine atom is preferable.

An aryl group having 6 to 10 carbon atoms, in $R_1$ to $R_3$ of the compound represented by the general formula (I), includes a phenyl group or a naphthyl group, and a phenyl group is preferable.

A halogeno group, as a substituent of the aryl group having 6 to 10 carbon atoms in $R_1$ to $R_3$, includes a fluoro group, a chloro group, a bromo group, an iodo group or the like, and a fluoro group is preferable.

An alkyl group as a substituent of the aryl group having 6 to 10 carbon atoms in $R_1$ to $R_3$ is usually an alkyl group having 1 to 6 carbon atoms, and is preferably an alkyl group having 1 to 4 carbon atoms, and may be any of a linear, branched or cyclic group. It specifically includes, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a n-hexyl group, an isohexyl group, a sec-hexyl group, a tert-hexyl group, a 3-methylpentyl group, a 2-methylpentyl group, a 1,2-dimethylbutyl group, a cyclopentyl group, a cyclohexyl group or the like, and a methyl group, an ethyl group, a n-propyl group and a n-butyl group are preferable, and a methyl group is more preferable.

A halogenoalkyl group as a substituent of the aryl group having 6 to 10 carbon atoms in $R_1$ to $R_3$ may be any of a linear, branched or cyclic group, and a linear group is preferable, and is usually a group having 1 to 6 carbon atoms, and is preferably a group having 1 to 3 carbon atoms. It specifically includes a fluoroalkyl group, a chloroalkyl group, a bromoalkyl group or the like, a fluoroalkyl group is preferable, and among them, a perfluoroalkyl group is particularly preferable. More specifically, it includes, for example, a fluoromethyl group, a perfluoromethyl group, a fluoroethyl group, a perfluoroethyl group, a fluoro-n-propyl group, a perfluoro-n-propyl group, a fluoro-n-butyl group, a perfluoro-n-butyl group, a fluoro-n-pentyl group, a perfluoro-n-pentyl group, a fluoro-n-hexyl group, a perfluoro-n-hexyl group, a chloromethyl group, a perchloromethyl group, a chloroethyl group, a perchloroethyl group, a chloro-n-propyl group, a perchloro-n-propyl group, a chloro-n-butyl group, a perchloro-n-butyl group, a chloro-n-pentyl group, a perchloro-n-pentyl group, a chloro-n-hexyl group, a perchloro-n-hexyl group, a bromomethyl group, a perbromomethyl group, a bromoethyl group, a perbromoethyl group, a bromo-n-propyl group, a perbromo-n-propyl group, a bromo-n-butyl group, a perbromo-n-butyl group, a bromo-n-pentyl group, a perbromo-n-pentyl group, a bromo-n-hexyl group, a perbromo-n-hexyl group or the like, and among them, a perfluoromethyl group, a perfluoroethyl group, a perfluoro-n-propyl group, a perfluoro-n-butyl group, a perfluoro-n-pentyl group and a perfluoro-n-hexyl group are preferable, and a perfluoromethyl group, a perfluoroethyl group and a perfluoro-n-propyl group are more preferable.

An alkoxy group as a substituent of the aryl group having 6 to 10 carbon atoms in $R_1$ to $R_3$ is usually a group having 1 to 6 carbon atoms, and is preferably a group having 1 to 4 carbon atoms, and specifically includes, for example, a methoxy group, an ethoxy group, a n-propoxy group, an isopropoxy group, a n-butoxy group, an isobutoxy group, a sec-butoxy group, a tert-butoxy group, a n-pentyloxy group, a n-hexyloxy group or the like, and a methoxy group, an ethoxy group, a n-propoxy group, an isopropoxy group, a tert-butoxy group or the like, is preferable.

An aryl group having 6 to 10 carbon atoms, which may have a halogeno group, an alkyl group, a halogenoalkyl group or an alkoxy group, as a substituent in $R_1$ to $R_3$ is preferably an aryl group which has a halogeno group, as a substituent, an aryl group which has an alkyl group as a substituent, an aryl group which has an alkoxy group as a substituent, an unsubstituted aryl group or the like. In addition, number of the substituents in the aryl group having 6 to 10 carbon atoms, which has the halogeno group, the alkyl group, the halogenoalkyl group or the alkoxy group, as a substituent in $R_1$ to $R_3$ is usually 1 to 7 pieces, preferably 1 to 5 pieces, and more preferably 1 to 2 pieces.

The aryl group having 6 to 10 carbon atoms, which may have a halogeno group, an alkyl group, a halogenoalkyl group or an alkoxy group, as a substituent in $R_1$ to $R_3$ specifically includes, for example, a phenyl group, a naphthyl group; a fluorophenyl group, a chlorophenyl group, a bromophenyl group, an iodophenyl group, a perfluorophenyl group, a perchlorophenyl group, a perbromophenyl group, a periodophenyl group; a methylphenyl group, an ethylphenyl group, a n-propylphenyl group, an isopropylphenyl group, a n-butylphenyl group, an isobutylphenyl group, a sec-butylphenyl group, a tert-butylphenyl group, a n-pentylphenyl group, an isopentylphenyl group, a sec-pentylphenyl group, a tert-pentylphenyl group, a neopentylphenyl group, a n-hexylphenyl group, an isohexylphenyl group, a sec-hexylphenyl group, a tert-hexylphenyl group, a 3-methylpentylphenyl group, a 2-methylpentylphenyl group, a 1,2-dimethylbutylphenyl group, a cyclopropylphenyl group, a cyclopentylphenyl group, a cyclohexylphenyl group; a fluoromethylphenyl group, a perfluoromethylphenyl group, a fluoroethylphenyl group, a perfluoroethylphenyl group, a fluoro-n-propylphenyl group, a perfluoro-n-propylphenyl group, a fluoroisopropylphenyl group, a perfluoroisopropylphenyl group, a fluoro-n-butylphenyl group, a perfluoro-n-butylphenyl group, a fluoroisobutylphenyl group, a perfluoroisobutylphenyl group, a fluoro-sec-butylphenyl group, a perfluoro-sec-butylphenyl group, a fluoro-tert-butylphenyl group, a perfluoro-tert-butylphenyl group, a fluoro-n-pentylphenyl group, a perfluoro-n-pentylphenyl group, a fluoroisopentylphenyl group, a perfluoroisopentylphenyl group, a fluoro-sec-pentylphenyl group, a perfluoro-sec-pentylphenyl group, a fluoro-tert-pentylphenyl group, a perfluoro-tert-butylphenyl group, a fluoroneopentylphenyl group, a perfluoroneopentylphenyl group, a fluoro-n-hexylphenyl group, a perfluoro-n-hexylphenyl group, a fluoroisohexylphenyl group, a perfluoroisohexylphenyl group, a fluoro-sec-hexylphenyl group, a perfluoro-sec-hexylphenyl group, a fluoro-tert-hexylphenyl group, a perfluoro-tert-hexylphenyl group, a fluoro-3-methylpentylphenyl group, a perfluoro-3-methylpentylphenyl group, a fluoro-2-methylpentylphenyl group, a perfluoro-2-methylpentylphenyl group, a fluoro-1,2-dimethylbutylphenyl group, a perfluoro-1,2-dimethylbutylphenyl group, a fluorocyclopropylphenyl group, a perfluorocyclopropylphenyl group, a fluorocyclobutylphenyl group, a perfluorocyclobutylphenyl group, a fluorocyclopentylphenyl group, a perfluorocyclopentylphenyl group, a fluorocyclohexylphenyl group, a perfluorocyclohexylphenyl group, a chloromethylphenyl group, a perchloromethylphenyl group, a chloroethylphenyl group, a perchloroethylphenyl group, a chloro-n-propylphenyl group, a perchloro-n-propylphenyl group, a chloroisopropylphenyl group, a perchloroisopropylphenyl group, a chloro-n-butylphenyl group, a perchloro-n-butylphenyl group, a chloroisobutylphenyl group, a perchloroisobutylphenyl group, a chloro-sec-butylphenyl group, a perchloro-sec-butylphenyl group, a chloro-tert-butylphenyl group, a perchloro-tert-butylphenyl group, a chloro-n-pentylphenyl group, a perchloro-n-pentylphenyl group, a chloroisopentylphenyl group, a perchloroisopentylphenyl group, a chloro-sec-pentylphenyl group, a perchloro-sec-pentylphenyl group, a chloro-tert-pentylphenyl group, a perchloro-tert-butylphenyl group, a chloroneopentylphenyl group, a perchloroneopentylphenyl group, a chloro-n-hexylphenyl group, a perchloro-n-hexylphenyl group, a chloroisohexylphenyl group, a perchloroisohexylphenyl group, a chloro-sec-hexylphenyl group, a perchloro-sec-hexylphenyl group, a chloro-tert-hexylphenyl group, a perchloro-tert-hexylphenyl group, a chloro-3-methylpentylphenyl group, a perchloro-3-methylpentylphenyl group, a chloro-2-methylpentylphenyl group, a perchloro-2-methylpentylphenyl group, a chloro-1,2-dimethylbutylphenyl group, a perchloro-1,2-dimethylbutylphenyl group, a chlorocyclopropylphenyl group, a perchlorocyclopropylphenyl group, a chlorocyclobutylphenyl group, a perchlorocyclobutylphenyl group, a chlorocyclopentylphenyl group, a perchlorocyclopentylphenyl group, a chlorocyclohexylphenyl group, a perchlorocyclohexylphenyl group, a bromomethylphenyl group, a perbromomethylphenyl group, a bromoethylphenyl group, a perbromoethylphenyl group, a bromo-n-propylphenyl group, a perbromo-n-propylphenyl group, a bromoisopropylphenyl group, a perbromoisopropylphenyl group, a bromo-n-butylphenyl group, a perbromo-n-butylphenyl group, bromoisobutylphenyl group, a perbromoisobutylphenyl group, a bromo-sec-butylphenyl group, a perbromo-sec-butylphenyl group, a bromo-tert-butylphenyl group, a perbromo-tert-butylphenyl group, a bromo-n-pentylphenyl group, a perbromo-n-pentylphenyl group, a bromoisopentylphenyl group, a perbromoisopentylphenyl group, a bromo-sec-pentylphenyl group, a perbromo-sec-pentylphenyl group, a bromo-tert-pentylphenyl group, a perbromo-tert-butylphenyl group, a bromoneopentylphenyl group, a perbromoneopentylphenyl group, a bromo-n-hexylphenyl group, a perbromo-n-hexylphenyl group, a bromoisohexylphenyl group, a perbromoisohexylphenyl group, a bromo-sec-hexylphenyl group, a perbromo-sec-hexylphenyl group, a bromo-tert-hexylphenyl group, a perbromo-tert-hexylphenyl group, a bromo-3-methylpentylphenyl group, a perbromo-3-methylpentylphenyl group, a bromo-2-methylpentylphenyl group, a perbromo-2-methylpentylphenyl group, a bromo-1,2-dimethylbutylphenyl group, a perbromo-1,2-dimethylbutylphenyl group, a bromocyclopropylphenyl group, a perbromocyclopropylphenyl group, a bromocyclobutylphenyl group, a perbromocyclobutylphenyl group, a bromocyclopentylphenyl group, a perbromocyclopentylphenyl group, a bromocyclohexylphenyl group, a perbromocyclohexylphenyl group; a methoxyphenyl group, an ethoxyphenyl group, a n-propoxyphenyl group, an isopropoxyphenyl group, a n-butoxyphenyl group, an isobutoxyphenyl group, a sec-butoxyphenyl group, a tert-butoxyphenyl group, a n-pentyloxyphenyl group, an isopentyloxyphenyl group, a sec-pentyloxyphenyl group, a tert-pentyloxyphenyl group, a neopentyloxyphenyl group, a n-hexyloxyphenyl group, an isohexyloxyphenyl group, a sec-hexyloxyphenyl group, a tert-hexyloxyphenyl group, a 3-methylpentyloxyphenyl group, a 2-methylpentyloxyphenyl group, a 1,2-dimethylbutoxyphenyl group, a cyclopropyloxyphenyl group, a cyclobutyloxyphenyl group, a cyclopentyloxyphenyl group, a cyclohexyloxyphenyl group or the like.

Among the above-described specific examples, a phenyl group, a methylphenyl group, an ethylphenyl group, a n-propylphenyl group, an isopropylphenyl group, a n-butylphenyl group, an isobutylphenyl group, a sec-butylphenyl group, a tert-butylphenyl group, a n-pentylphenyl group, an isopentylphenyl group, a sec-pentylphenyl group, a tert-pentylphenyl group, a neopentylphenyl group, a n-hexylphenyl group, an isohexylphenyl group, a sec-hexylphenyl group, a tert-hexylphenyl group, a 3-methylpentylphenyl group, a 2-methylpentylphenyl group, a 1,2-dimethylbutylphenyl group, a cyclopropylphenyl group, a cyclopentylphenyl group, a cyclohexylphenyl group; a fluoromethylphenyl group, a perfluoromethylphenyl group, a fluoroethylphenyl group, a perfluoroethylphenyl group, a fluoro-n-propylphenyl group, a perfluoro-n-propylphenyl group, a fluoro-n-butylphenyl group, a perfluoro-n-butylphenyl group, a fluoro-n-pentylphenyl group, a perfluoro-n-pentylphenyl group, a fluoro-n-hexylphenyl group, a perfluoro-n-hexylphenyl group, a chloromethylphenyl group, a perchloromethylphenyl group, a chloroethylphenyl group, a perchloroethylphenyl group, a chloro-n-propylphenyl group, a perchloro-n-propylphenyl group, a chloro-n-butylphenyl group, a perchloro-n-butylphenyl group, a chloro-n-pentylphenyl group, a perchloro-n-pentylphenyl group, a chloro-n-hexylphenyl group, a perchloro-n-hexylphenyl group, a bromomethylphenyl group, a perbromomethylphenyl group, a bromoethylphenyl group, a perbromoethylphenyl group, a bromo-n-propylphenyl group, a perbromo-n-propylphenyl group, a bromo-n-butylphenyl group, a perbromo-n-butylphenyl group, a bromo-n-pentylphenyl group, a perbromo-n-pentylphenyl group, a bromo-n-hexylphenyl group, a perbromo-n-hexylphenyl group; a methoxyphenyl group, an ethoxyphenyl group, a n-propoxyphenyl group, an isopropoxyphenyl group, a n-butoxyphenyl group, an isobutoxyphenyl group, a sec-butoxyphenyl group, a tert-butoxyphenyl group, a n-pentyloxyphenyl group, a n-hexyloxyphenyl group and the like are preferable, and a phenyl group, a methylphenyl group, an ethylphenyl group, a n-propylphenyl group, an isopropylphenyl group; a fluoromethylphenyl group, a chloromethylphenyl group, a bromomethylphenyl group, an iodomethylphenyl group; a methoxyphenyl group, an ethoxyphenyl group, a n-propoxyphenyl group, an isopropoxyphenyl group, a tert-butoxyphenyl group and the like, are more preferable.

An alkenyl group having 1 to 6 carbon atoms, in $R_2$ and $R_3$ of the compound represented by the general formula (I), may be any of a linear, branched or cyclic group, and the group having 1 to 3 carbon atoms is preferable. It specifically includes, for example, a vinyl group, an allyl group, a 1-propenyl group, an isopropenyl group, a 3-butenyl group, a 2-butenyl group, a 1-butenyl group, a 1,3-butadienyl group, a 4-pentenyl group, a 3-pentenyl group, a 2-pentenyl group, a 1-pentenyl group, a 1-methyl-1-butenyl group, a 5-hexenyl group, a 4-hexenyl group, a 3-hexenyl group, a 2-hexenyl group, a 1-hexenyl group or the like, and among them, a vinyl group, an allyl group, a 1-propenyl group and an isopropenyl group are preferable, and an allyl group is more preferable.

An alkyl group having 1 to 6 carbon atoms, in $R_2$ and $R_3$ of the compound represented by the general formula (I), is preferably a group having 1 to 4 carbon atoms, and may be any of a linear, branched or cyclic group, and specifically includes, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a n-hexyl group, an isohexyl group, a sec-hexyl group, a tert-hexyl group, a 3-methylpentyl group, a 2-methylpentyl group, a 1,2-dimethylbutyl group, a cyclopentyl group, a cyclohexyl group or the like, and a methyl group, an ethyl group, a n-propyl group and a n-butyl group are preferable.

A halogeno group as a substituent of the alkyl group, having 1 to 6 carbon atoms, in $R_2$ and $R_3$ includes, a fluoro group, a chloro group, a bromo group, an iodo group or the like, and a fluoro group is preferable.

An alkoxy group as a substituent of the alkyl group having 1 to 6 carbon atoms, in $R_1$ to $R_3$, is usually a group having 1 to 6 carbon atoms, and is preferably a group having 1 to 3 carbon atoms, and specifically includes, for example, a methoxy group, an ethoxy group, a n-propoxy group, an isopropoxy group, a n-butoxy group, an isobutoxy group, a sec-butoxy group, a tert-butoxy group, a n-pentyloxy group, a n-hexyloxy group or the like, and a methoxy group, an ethoxy group, a n-propoxy group, an isopropoxy group or the like is preferable.

The alkyl group having 1 to 6 carbon atoms, which may have a halogeno group or an alkoxy group, as a substituent, in $R_1$ to $R_3$, specifically includes, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a n-hexyl group, an isohexyl group, a sec-hexyl group, a tert-hexyl group, a 3-methylpentyl group, a 2-methylpentyl group, a 1,2-dimethylbutyl group, a cyclopentyl group, a cyclohexyl group; a perfluoromethyl group, a perfluoroethyl group, a perfluoro-n-propyl group, a perfluoroisopropyl group, a perfluoro-n-butyl group, a perfluoroisobutyl group, a perfluoro-sec-butyl group, a perfluoro-tert-butyl group, a perfluoro-n-pentyl group, a perfluoroisopentyl group, a perfluoro-sec-pentyl group, a perfluoro-tert-pentyl group, a perfluoroneopentyl group, a perfluoro-n-hexyl group, a perfluoroisohexyl group, a perfluoro-sec-hexyl group, a perfluoro-tert-hexyl group, a perfluoro-3-methylpentyl group, a perfluoro-2-methylpentyl group, a perfluoro-1,2-dimethylbutyl group, a perfluorocyclopentyl group, a perfluorocyclohexyl group, a fluoromethyl group, a fluoroethyl group, a fluoro-n-propyl group, a fluoroisopropyl group, a fluoro-n-butyl group, a fluoroisobutyl group, a fluoro-sec-butyl group, a fluoro-tert-butyl group, a fluoro-n-pentyl group, a fluoroisopentyl group, a fluoro-sec-pentyl group, a fluoro-tert-pentyl group, a fluoroneopentyl group, a fluoro-n-hexyl group, a fluoroisohexyl group, a fluoro-sec-hexyl group, a fluoro-tert-hexyl group, a fluoro-3-methylpentyl group, a fluoro-2-methylpentyl group, a fluoro-1,2-dimethylbutyl group, a fluorocyclopentyl group, a fluorocyclohexyl group; a perchloromethyl group, a perchloroethyl group, a perchloro-n-propyl group, a perchloroisopropyl group, a perchloro-n-butyl group, a perchloro-sec-butyl group, a perchloro-tert-butyl group, a perchloro-n-pentyl group, a perchloroisopentyl group, a perchloro-sec-pentyl group, a perchloro-tert-pentyl group, a perchloroneopentyl group, a perchloro-n-hexyl group, a perchloroisohexyl group, a perchloro-sec-hexyl group, a perchloro-tert-hexyl group, a perchloro-3-methylpentyl group, a perchloro-2-methylpentyl group, a perchloro-1,2-dimethylbutyl group, a perchlorocyclopentyl group, a perchlorocyclohexyl group, a chloromethyl group, a chloroethyl group, a chloro-n-propyl group, a chloroisopropyl group, a chloro-n-butyl group, a chloroisobutyl group, a chloro-sec-butyl group, a chloro-tert-butyl group, a chloro-n-pentyl group, a chloroisopentyl group, a chloro-sec-pentyl group, a chloro-tert-pentyl group, a chloroneopentyl group, a chloro-n-hexyl group, a chloroisohexyl group, a chloro-sec-hexyl group, a chloro-tert-hexyl group, a chloro-3-methylpentyl group, a chloro-2-methylpentyl group, a chloro-1,2-dimethylbutyl group, a chlorocyclopentyl group, a chlorocyclohexyl group; a perbromomethyl group, a perbromoethyl group, a perbromo-n-propyl group, a perbromoisopropyl group, a perbromo-n-butyl group, a perbromo-sec-butyl group, a perbromo-tert-butyl group, a perbromo-n-pentyl group, a perbromoisopentyl group, a perbromo-sec-pentyl group, a perbromo-tert-pentyl group, a perbromoneopentyl group, a perbromo-n-hexyl group, a perbromoisohexyl group, a perbromo-sec-hexyl group, a perbromo-tert-hexyl group, a perbromo-3-methylpentyl group, a perbromo-2-methylpentyl group, a perbromo-1,2-dimethylbutyl group, a perbromocyclopentyl group, a perbromocyclohexyl group, a bromomethyl group, a bromoethyl group, a bromo-n-propyl group, a bromoisopropyl group, a bromo-n-butyl group, a bromoisobutyl group, a bromo-sec-butyl group, a bromo-tert-butyl group, a bromo-n-pentyl group, a bromoisopentyl group, a bromo-sec-pentyl group, a bromo-tert-pentyl group, a bromoneopentyl group, a bromo-n-hexyl group, a bromoisohexyl group, a bromo-sec-hexyl group, a bromo-tert-hexyl group, a bromo-3-methylpentyl group, a bromo-2-methylpentyl group, a bromo-1,2-dimethylbutyl group, a bromocyclopentyl group, a bromocyclohexyl group; a periodomethyl group, a periodoethyl group, a periodo-n-propyl group, a periodoisopropyl group, a periodo-n-butyl group, a periodo-sec-butyl group, a periodo-tert-butyl group, a periodo-n-pentyl group, a periodoisopentyl group, a periodo-sec-pentyl group, a periodo-tert-pentyl group, a periodoneopentyl group, a periodo-n-hexyl group, a periodoisohexyl group, a periodo-sec-hexyl group, a periodo-tert-hexyl group, a periodo-3-methylpentyl group, a periodo-2-methylpentyl group, a periodo-1,2-dimethylbutyl group, a periodocyclopentyl group, a periodocyclohexyl group, an iodomethyl group, an iodoethyl group, an iodo-n-propyl group, an iodoisopropyl group, an iodo-n-butyl group, an iodoisobutyl group, an iodo-sec-butyl group, an iodo-tert-butyl group, an iodo-n-pentyl group an iodoisopentyl group, an iodo-sec-pentyl group, an iodo-tert-pentyl group, an iodoneopentyl group, an iodo-n-hexyl group, an iodoisohexyl group, an iodo-sec-hexyl group, an iodo-tert-hexyl group, an iodo-3-methylpentyl group, an iodo-2-methylpentyl group, an iodo-1,2-dimethylbutyl group, an iodocyclopentyl group, an iodocyclohexyl group; a methoxymethyl group, an ethoxymethyl group, a n-propoxymethyl group, an isopropoxymethyl group, a n-butoxymethyl group, an isobutoxymethyl group, a sec-butoxymethyl group, a tert-butoxymethyl group, a n-pentyloxymethyl group, a neopentyloxymethyl group, a n-hexyloxymethyl group, a methoxyethyl group, an ethoxyethyl group, a n-propoxyethyl group, an isopropoxyethyl group, a n-butoxyethyl group, an isobutoxyethyl group, a sec-butoxyethyl group, a tert-butoxyethyl group, a n-pentyloxyethyl group, a neopentyloxyethyl group, a n-hexyloxyethyl group, a methoxy-n-propyl group, an ethoxy-n-propyl group, a n-propoxy-n-propyl group, an isopropoxy-n-propyl group, a n-butoxy-n-propyl group, an isobutoxy-n-propyl group, a sec-butoxy-n-propyl group, a tert-butoxy-n-propyl group, a n-pentyloxy-n-propyl group, a neopentyloxy-n-propyl group, a n-hexyloxy-n-propyl group, a methoxy-n-butyl group, an ethoxy-n-butyl group, a n-propoxy-n-butyl group, an isopropoxy-n-butyl group, a n-butoxy-n-butyl group, an isobutoxy-n-butyl group, a sec-butoxy-n-butyl group, a tert-butoxy-n-butyl group, a n-pentyloxy-n-butyl group, a neopentyloxy-n-butyl group, a n-hexyloxy-n-butyl group or the like.

Among these, a perfluoromethyl group, a perfluoroethyl group, a perfluoro-n-propyl group, a perfluoroisopropyl group, a perfluoro-n-butyl group, a perfluoro-sec-butyl group, a perfluoro-tert-butyl group, a methoxymethyl group, an ethoxymethyl group, a methoxyethyl group, an ethoxyethyl group or the like, is preferable.

$R_2$ and $R_3$ in the compound represented by the general formula (I) is preferably a magnesium chloride oxy group (—OMgCl); an alkenyl group having 1 to 6 carbon atoms; an alkyl group having 1 to 6 carbon atoms; or an aryl group having 6 to 10 carbon atoms, which may have a halogeno group, an alkyl group, a halogenoalkyl group or an alkoxy group, as a substituent, and more preferably, a magnesium chloride oxy group (—OMgCl); an alkenyl group having 1 to 6 carbon atoms; an alkyl group having 1 to 6 carbon atoms; or an aryl group having 6 to 10 carbon atoms, which may have an alkyl group, as a substituent. Preferable specific examples thereof include a magnesium chloride oxy group (—OMgCl), a vinyl group, an allyl group, a 1-propenyl group, an isopropenyl group, a methyl group, an ethyl group, a n-propyl group, a n-butyl group, a phenyl group, a methylphenyl group, an ethylphenyl group, a n-propylphenyl group, an isopropylphenyl group; a fluoromethylphenyl group, a chloromethylphenyl group, a bromomethylphenyl group, an iodomethylphenyl group; a methoxyphenyl group, an ethoxyphenyl group, a n-propoxyphenyl group, an isopropoxyphenyl group, a tert-butoxyphenyl group or the like, and a magnesium chloride oxy group (—OMgCl), a vinyl group, an allyl group, a 1-propenyl group, an isopropenyl group, a methyl group, an ethyl group, a n-propyl group, a n-butyl group, a phenyl group, a methylphenyl group, an ethylphenyl group, a n-propylphenyl group, an isopropylphenyl group or the like, is more preferable.

Preferable specific examples of the compound represented by the general formula (I) include compounds represented by the following general formulae (I-I), (I-II) or (I-III).

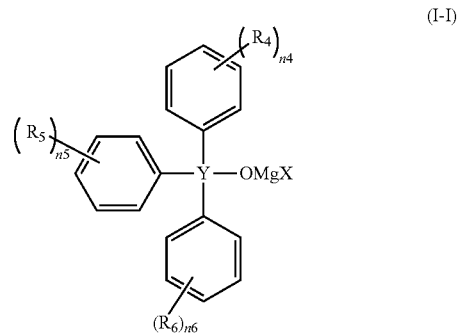

(I-I)

(wherein $R_4$, $R_5$ and $R_6$ each independently represent a halogeno group, an alkyl group, a halogenoalkyl group or an alkoxy group, n4, n5 and n6 each independently represent an integer of 0 to 5, and X and Y are the same as described above.)

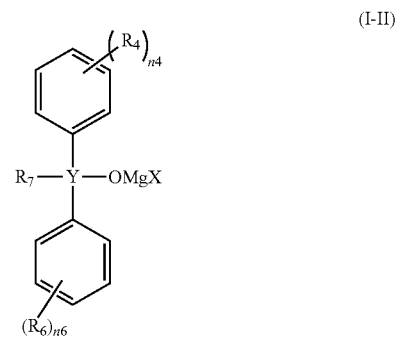

(I-II)

(wherein $R_7$ represents a magnesium chloride oxy group (—OMgCl), an alkenyl group having 1 to 6 carbon atoms or an alkyl group having 1 to 6 carbon atoms, and $R_4$, $R_6$, n4, n6, X and Y are the same as described above.)

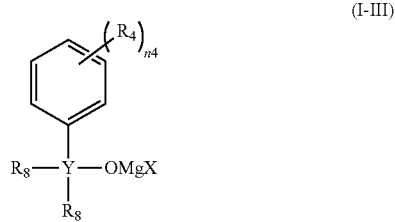

(I-III)

(wherein two pieces of $R_8$ each independently represent a magnesium chloride oxy group (—OMgCl), an alkenyl group having 1 to 6 carbon atoms or an alkyl group having 1 to 6 carbon atoms, and $R_4$, n4, X and Y are the same as described above.)

In the compounds represented by (I-I), (I-II) or (I-III), Y is preferably a silicon atom. In addition, X is preferably a chlorine atom.

As a halogeno group, an alkyl group, a halogenoalkyl group or an alkoxy group in the above-described $R_4$, $R_5$, and $R_6$, a halogeno group, an alkyl group or an alkoxy group is preferable. Specific examples thereof include a same group as described as a substituent of the aryl group having 6 to 10 carbon atoms in the above-described $R_1$ to $R_3$, and a preferable group is also the same.

As the above-described n4, n5, and n6, 0 to 2 is preferable.

Specific examples of an alkenyl group having 1 to 6 carbon atoms and an alkyl group having 1 to 6 carbon atoms in the above-described $R_7$ and $R_8$ include a same group as the alkenyl group having 1 to 6 carbon atoms and the alkyl group having 1 to 6 carbon atoms in the $R_2$ and $R_3$, respectively, and a preferable group is also the same.

As $R_7$, a magnesium chloride oxy group (—OMgCl) or an alkenyl group having 1 to 6 carbon atoms is preferable. As $R_8$, an alkyl group having 1 to 6 carbon atoms is preferable.

[Lewis Acid]

Lewis acid relating to the present invention is Lewis acid which contains beryllium (Be), boron (B), aluminum (Al), silicon (Si), tin (Sn), titanium (Ti), chromium (Cr), iron (Fe), cobalt (Co), as an element. It specifically includes, a beryllium compound, such as beryllium (II) fluoride, beryllium (II) chloride, beryllium (II) bromide or the like; a boron compound, such as boron (III) chloride, boron (III) fluoride, boron (III) bromide, triphenoxyborane, phenyldichloroborane, triphenylborane or the like; an aluminum compound, such as aluminum (III) chloride, aluminum (III) bromide, aluminum (III) iodide, dimethylaluminum chloride, diethylaluminum chloride, methylaluminum dichloride, ethylaluminum dichloride, trimethylaluminum, triethylaluminum or the like; a silyl compound, such as trimethylsilyl triflate, trimethylsilyl iodide, tert-butyldimethylsilyl triflate or triisopropylsilyl triflate or the like; a tin compound, such as tin (IV) chloride, tin (IV) bromide, tin (II) chloride, tin (II) triflate or the like; a titanium compound, such as titanium (IV) chloride, titanium (IV) fluoride, titanium (IV) bromide, titanium (IV) iodide or the like; a chromium compound, such as chromium (II) fluoride, chromium (III) fluoride, chromium (II) chloride, chromium (III) chloride, chromium (II) bromide, chromium (III) bromide, chromium (II) iodide, chromium (III) iodide or the like; an iron compound, such as iron (II) fluoride, iron (II) chloride, iron (III) chloride, iron (II) bromide, iron (II) iodide or the like; or a cobalt compound, such as cobalt (II) fluoride, cobalt (II) chloride, cobalt (II) bromide, cobalt (II) iodide or the like.

Among them, a boron compound or an aluminum compound is preferable, and an aluminum compound is more preferable. Specifically, aluminum (III) chloride, methylaluminum dichloride, dimethylaluminum chloride, boron (III) chloride or the like, is preferable, and aluminum (III) chloride is particularly preferable.

[Solvent]

A solvent relating to the present invention is preferably a solvent which is capable of dissolving the compound represented by the general formula (I) relating to the present invention. Such a solvent includes, for example, an ether-type solvent, a halogenated hydrocarbon-type solvent, a carbonate-type solvent, a nitrile-type solvent, a sulfone-type solvent or the like.

The ether-type solvent includes, for example, diethyl ether, diglyme, triglyme, tetraglyme, tetrahydrofuran, 2-methyltetrahydrofuran, diisopropyl ether, 1,2-dimethoxyethane, diethylene glycol dimethyl ether, triethylene glycol dimethyl ether, cyclopentyl methyl ether, t-butyl methyl ether, 1,4-dioxane or the like; the halogenated hydrocarbon-type solvent includes, for example, dichloromethane, chloroform, carbon tetrachloride, 1,2-dichloroethane or the like; the carbonate-type solvent includes, for example, dimethyl carbonate, diethyl carbonate, ethyl methyl carbonate, propylene carbonate or the like; the nitrile-type solvent includes, for example, acetonitrile, propionitrile, butyronitrile, succinonitrile, pimelonitrile, methoxypropionitrile or the like; and the sulfone-type solvent includes, for example, sulfolane, dimethyl sulfone, ethyl methyl sulfone, methyl n-propyl sulfone, methyl isopropyl sulfone, n-butyl methyl sulfone, isobutyl methyl sulfone, sec-butyl methyl sulfone, tert-butyl methyl sulfone, diethyl sulfone, ethyl n-propyl sulfone, ethyl isopropyl sulfone, n-butyl ethyl sulfone, isobutyl ethyl sulfone, sec-butyl ethyl sulfone, tert-butyl ethyl sulfone, di-n-propyl sulfone, diisopropyl sulfone, n-butyl n-propyl sulfone, di-n-butyl sulfone or the like.

Among the specific examples, the ether-type solvent, the sulfone-type solvent or the like, is preferable, and specifically, 1,2-dimethoxyethane, diglyme, triglyme, tetraglyme, tetrahydrofuran and sulfolane are particularly preferable, and diglyme, triglyme, tetraglyme and tetrahydrofuran are particularly preferable.

The solvent relating to the present invention may be solvents in which two or more kinds of the solvent are mixed.

[Electrolytic Solution]

The electrolytic solution of the present invention comprises a mixture obtained by mixing the compound represented by the general formula (I) relating to the present invention and the Lewis acid relating to the present invention, in the solvent relating to the present invention.

Concentration of the compound represented by the general formula (I) in the electrolytic solution is usually 0.1 to 5 mol/mL, preferably 0.1 to 3 mol/mL and more preferably 0.2 to 2 mol/mL.

Amount of the Lewis acid to be used in the electrolytic solution of the present invention is usually 0.1 to 5 times mol and preferably 0.1 to 3 times mol, relative to the compound represented by the general formula (I) relating to the present invention.

The electrolytic solution of the present invention may contain additives, such as a film-forming ingredient, an overcharge inhibitor, an oxygen scavenger, a dehydrating agent, a flame retardant and the like, usually used in this field, and additives having coordinating property, such as a crown ether and the like.

Such an electrolytic solution of the present invention can be used in a magnesium battery, and in the case of a magnesium secondary battery, exhibits high oxidation decomposition potential, and can be used repeatedly and stably.

The electrolytic solution of the present invention is produced by dissolving (mixing) the compound represented by the general formula (I) relating to the present invention and the Lewis acid relating to the present invention, in the solvent pertaining to the present invention. In more specifically, it is produced by using 0.1 to 5 mol of the Lewis acid relating to the present invention, relative to 1 mol of the compound represented by the general formula (I) relating to the present invention, and by the addition and mixing of these into the solvent relating to the present invention to attain the concentration. It should be noted that, in mixing, it may be heated or cooled in a range of −78 to 300° C., and preferably 0 to 70° C., as needed.

[Electrochemical Device]

The electrochemical device of the present invention comprises a positive electrode, a negative electrode and the electrolytic solution of the present invention. Specifically, it includes a primary battery, a secondary battery, an electric double layer capacitor or the like, and among them, a secondary battery is preferable.

The positive electrode in the electrochemical device of the present invention is not especially limited, if it is an electrode capable of containing magnesium or a magnesium ion inside thereof, or on the surface and at the vicinity thereof. Specifically, for example, it includes an electrode containing an oxide, or a sulfide containing cobalt, manganese, vanadium, aluminum, iron, silicon, phosphorous, nickel, molybdenum, titanium or the like, as an active material.

In addition, in the positive electrode, such materials may be contained as an active material which is capable of adsorbing and storing magnesium or the magnesium ion, such as sulfur or the like; organic chemicals having high oxidizability; a material forming an electric double layer capacitor, such as porous carbon, an activated carbon or the like, and magnesium may be contained in an oxidized form.

The negative electrode in the electrochemical device of the present invention is not especially limited, if it is an electrode capable of containing magnesium or the magnesium ion inside thereof, or on the surface and at the vicinity thereof. Specifically, for example, it includes metal magnesium or magnesium alloys, which is capable of dissolving and depositing magnesium; metal which can be alloyed with magnesium which is capable of dissolving and depositing magnesium; a carbon material which is capable of intercalating magnesium or a magnesium ion; or the like.

In addition, the electrochemical device of the present invention may further have a separator, other than the positive electrode, the negative electrode and the electrolytic solution of the present invention. The separator may be any one if it electrically insulates the positive electrode and the negative electrode, and is capable of permeating a magnesium ion; and includes, for example, a microporous polymeric film, such as a porous polyolefin film or the like. Specific examples of the porous polyolefin film include, for example, a single-layered porous polyolefin film, or a multi-layered film, where a porous polyethylene film and a porous polypropylene film are laminated.

[Compound Represented by the General Formula (I')]

X of the compound represented by the general formula (I') represents a chlorine atom or a bromine atom, and a chlorine atom is preferable.

$R'_1$ in the compound represented by the general formula (I') represents an aryl group having 6 to 10 carbon atoms, which may have a halogeno group, an alkyl group, a halogenoalkyl group or an alkoxy group, as a substituent, and specific examples and preferable examples of the aryl group having 6 to 10 carbon atoms, which may have a halogeno group, an alkyl group, a halogenoalkyl group or an alkoxy group, as a substituent, include the same examples of $R_1$ in the compound represented by the general formula (I).

$R'_2$ and $R'_3$ in the compound represented by the general formula (I') each independently represent a magnesium chloride oxy group (—OMgCl); an alkenyl group having 1 to 6 carbon atoms; an alkyl group having 1 to 6 carbon atoms, which may have a halogeno group or an alkoxy group, as a substituent; or an aryl group having 6 to 10 carbon atoms, which may have a halogeno group, an alkyl group, a halogenoalkyl group or an alkoxy group, as a substituent. Specific examples and preferable examples of the alkenyl group having 1 to 6 carbon atoms, the alkyl group having 1 to 6 carbon atoms, which may have a halogeno group or an alkoxy group, as a substituent, as well as the aryl group having 6 to 10 carbon atoms, which may have a halogeno group, an alkyl group, a halogenoalkyl group or an alkoxy group, as a substituent, include the same examples of $R_2$ and $R_3$ in the compound represented by the general formula (I).

Preferable specific examples of $R'_2$ and $R'_3$ include the same examples of $R_2$ and $R_3$ in the compound represented by the general formula (I).

Specific examples of the compound represented by the general formula (I') include, for example, a magnesium bromide compound, and specifically include magnesium bromide triphenylsiloxide; magnesium bromide tris(2-methylphenyl)siloxide, magnesium bromide tris(3-methylphenyl)siloxide, magnesium bromide tris(4-methylphenyl)siloxide, magnesium bromide tris(2,2-dimethylphenyl)siloxide, magnesium bromide tris(3,3-dimethylphenyl)siloxide, magnesium bromide tris(2,3-dimethylphenyl)siloxide, magnesium bromide tris(2,4-dimethylphenyl)siloxide, magnesium bromide tris(3,4-dimethylphenyl)siloxide, magnesium bromide tris(2,4,6-trimethylphenyl)siloxide, magnesium bromide tris(2,3,4,5-tetramethylphenyl)siloxide, magnesium bromide tris(2,3,4,6-tetramethylphenyl)siloxide, magnesium bromide tris(2,3,5,6-tetramethylphenyl)siloxide, magnesium bromide tris(2,3,4,5,6-pentamethylphenyl)siloxide; magnesium bromide tris(2-fluorophenyl)siloxide, magnesium bromide tris(3-fluorophenyl)siloxide, magnesium bromide tris(4-fluorophenyl)siloxide, magnesium bromide tris(2,2-difluorophenyl)siloxide, magnesium bromide tris(3,3-difluorophenyl)siloxide, magnesium bromide tris(2,3-difluorophenyl)siloxide, magnesium bromide tris(2,4-difluorophenyl)siloxide, magnesium bromide tris(3,4-difluorophenyl)siloxide, magnesium bromide tris(2,4,6-trifluorophenyl)siloxide, magnesium bromide tris(2,3,4,5-tetrafluorophenyl)siloxide, magnesium bromide tris(2,3,4,6-tetrafluorophenyl)siloxide, magnesium bromide tris(2,3,5,6-tetrafluorophenyl)siloxide, magnesium bromide tris(2,3,4,5,6-pentafluorophenyl)siloxide; magnesium bromide tris(2-methoxyphenyl)siloxide, magnesium bromide tris(3-methoxyphenyl)siloxide, magnesium bromide tris(4-methoxyphenyl)siloxide, magnesium bromide tris(2,2-dimethoxyphenyl)siloxide, magnesium bromide tris(3,3-dimethoxyphenyl)siloxide, magnesium bromide tris(2,3-dimethoxyphenyl)siloxide, magnesium bromide tris(2,4-dimethoxyphenyl)siloxide, magnesium bromide tris(3,4-dimethoxyphenyl)siloxide, magnesium bromide tris(2,4,6- trimethoxyphenyl)siloxide, magnesium bromide tris(2,3,4,5-tetramethoxyphenyl)siloxide, magnesium bromide tris(2,3,4,6-tetramethoxyphenyl)siloxide, magnesium bromide tris(2,3,5,6-tetramethoxyphenyl)siloxide, magnesium bromide tris(2,3,4,5,6-pentamethoxyphenyl)siloxide; magnesium bromide dimethylphenylsiloxide, magnesium bromide methyldiphenylsiloxide, magnesium bromide diethylphenylsiloxide, magnesium bromide ethyldiphenylsiloxide, magnesium bromide di(tert-butyl)phenylsiloxide, magnesium bromide tert-butyldiphenylsiloxide; magnesium bromide dimethyl(methylphenyl)siloxide, magnesium bromide methyldi(methylphenyl)siloxide, magnesium bromide dimethyl(dimethylphenyl)siloxide, magnesium bromide methyldi(dimethylphenyl)siloxide, magnesium bromide dimethyl(trimethylphenyl)siloxide, magnesium bromide methyldi(trimethylphenyl)siloxide, magnesium bromide dimethyl(tetramethylphenyl)siloxide, magnesium bromide methyldi(tetramethylphenyl)siloxide, magnesium bromide dimethyl(pentamethylphenyl)siloxide, magnesium bromide methyldi(pentamethylphenyl)siloxide; magnesium bromide dimethyl(fluorophenyl)siloxide, magnesium bromide methyldi(fluorophenyl)siloxide, magnesium bromide dimethyl(difluorophenyl)siloxide, magnesium bromide methyldi(difluorophenyl)siloxide, magnesium bromide dimethyl(trifluorophenyl)siloxide, magnesium bromide methyldi(trifluorophenyl)siloxide, magnesium bromide dimethyl(tetrafluorophenyl)siloxide, magnesium bromide methyldi(tetrafluorophenyl)siloxide, magnesium bromide dimethyl(pentafluorophenyl)siloxide, magnesium bromide methyldi(pentafluorophenyl)siloxide; magnesium bromide dimethyl(methoxyphenyl)siloxide, magnesium bromide methyldi(methoxyphenyl)siloxide, magnesium bromide dimethyl(dimethoxyphenyl)siloxide, magnesium bromide methyldi(dimethoxyphenyl)siloxide, magnesium bromide dimethyl(trimethoxyphenyl)siloxide, magnesium bromide methyldi(trimethoxyphenyl)siloxide, magnesium bromide dimethyl(tetramethoxyphenyl)siloxide, magnesium bromide methyldi(tetramethoxyphenyl)siloxide, magnesium bromide dimethyl(pentamethoxyphenyl)siloxide, magnesium bromide methyldi(pentamethoxyphenyl)siloxide; magnesium bromide dimethyl(trifluoromethylphenyl)siloxide, magnesium bromide methyldi(trifluoromethylphenyl)siloxide, magnesium bromide dimethyl(di(trifluoromethyl)phenyl)siloxide, magnesium bromide methyldi(di(trifluoromethyl)phenyl)siloxide, magnesium bromide dimethyl(tri(trifluoromethyl)phenyl)siloxide, magnesium bromide methyldi(tri(trifluoromethyl)phenyl)siloxide, magnesium chloride dimethyl(tetra(trifluoromethyl)phenyl)siloxide, magnesium bromide methyldi(tetra(trifluoromethyl)phenyl)siloxide, magnesium bromide dimethyl(penta(trifluoromethyl)phenyl)siloxide, magnesium bromide methyldi(penta(trifluoromethyl)phenyl)siloxide, magnesium bromide di(tert-butyl)(trifluoromethylphenyl)siloxide, magnesium bromide methyldi(trifluoromethylphenyl)siloxide, magnesium bromide dimethyl(di(trifluoromethyl)phenyl)siloxide, magnesium bromide methyldi(di(trifluoromethyl)phenyl)siloxide, magnesium bromide dimethyl(tri(trifluoromethyl)phenyl)siloxide, magnesium bromide methyldi(tri(trifluoromethyl)phenyl)siloxide, magnesium bromide dimethyl(tetra(trifluoromethyl)phenyl)siloxide, magnesium bromide methyldi(tetra(trifluoromethyl)phenyl)siloxide, magnesium bromide dimethyl(penta(trifluoromethyl)phenyl)siloxide, magnesium bromide methyldi(penta(trifluoromethyl)phenyl)siloxide; diphenylsilanedioxy bis(magnesium bromide), di(methylphenyl)silanedioxy bis(magnesium bromide), di(dimethylphenyl)silanedioxy bis(magnesium bromide), di(trimethylphenyl)silanedioxy bis(magnesium bromide), di(tetramethylphenyl)silanedioxy bis(magnesium bromide), di(pentamethylphenyl)silanedioxy bis(magnesium bromide); di(fluorophenyl)silanedioxy bis(magnesium bromide), di(difluorophenyl)silanedioxy bis(magnesium bromide), di(trifluorophenyl)silanedioxy bis(magnesium bromide), di(tetrafluorophenyl)silanedioxy bis(magnesium bromide), di(pentafluorophenyl)silanedioxy bis(magnesium bromide); di(methoxyphenyl)silanedioxy bis(magnesium bromide), di(dimethoxyphenyl)silanedioxy bis(magnesium bromide), di(trimethoxyphenyl)silanedioxy bis(magnesium bromide), di(tetramethoxyphenyl)silanedioxy bis(magnesium bromide), di(pentamethoxyphenyl)silanedioxy bis(magnesium bromide); di(trifluoromethylphenyl)silanedioxy bis(magnesium bromide), di(di(trifluoromethyl)phenyl)silanedioxy bis(magnesium bromide), di(tri(trifluoromethyl)phenyl)silanedioxy bis(magnesium bromide), di(tetra(trifluoromethyl)phenyl)silanedioxy bis(magnesium bromide), di(penta(trifluoromethyl)phenyl)silanedioxy bis(magnesium bromide) or the like.

In addition, specific examples of the compound represented by the general formula (I') include, for example, a magnesium chloride compound, and specifically include magnesium chloride triphenylsiloxide; magnesium chloride tris(2-methylphenyl)siloxide, magnesium chloride tris(3-methylphenyl)siloxide, magnesium chloride tris(4-methylphenyl)siloxide, magnesium chloride tris(2,2-dimethylphenyl)siloxide, magnesium chloride tris(3,3-dimethylphenyl)siloxide, magnesium chloride tris(2,3-dimethylphenyl)siloxide, magnesium chloride tris(2,4-dimethylphenyl)siloxide, magnesium chloride tris(3,4-dimethylphenyl)siloxide, magnesium chloride tris(2,4,6-trimethylphenyl)siloxide, magnesium chloride tris(2,3,4,5-tetramethylphenyl)siloxide, magnesium chloride tris(2,3,4,6-tetramethylphenyl)siloxide, magnesium chloride tris(2,3,5,6-tetramethylphenyl)siloxide, magnesium chloride tris(2,3,4,5,6-pentamethylphenyl)siloxide; magnesium chloride tris(2-fluorophenyl)siloxide, magnesium chloride tris(3-fluorophenyl)siloxide, magnesium chloride tris(4-fluorophenyl)siloxide, magnesium chloride tris(2,2-difluorophenyl)siloxide, magnesium chloride tris(3,3-difluorophenyl)siloxide, magnesium chloride tris(2,3-difluorophenyl)siloxide, magnesium chloride tris(2,4-difluorophenyl)siloxide, magnesium chloride tris(3,4-difluorophenyl)siloxide, magnesium chloride tris(2,4,6-trifluorophenyl)siloxide, magnesium chloride tris(2,3,4,5-tetrafluorophenyl)siloxide, magnesium chloride tris(2,3,4,6-tetrafluorophenyl)siloxide, magnesium chloride tris(2,3,5,6-tetrafluorophenyl)siloxide, magnesium chloride tris(2,3,4,5,6-pentafluorophenyl)siloxide; magnesium chloride tris(2-methoxyphenyl)siloxide, magnesium chloride tris(3-methoxyphenyl)siloxide, magnesium chloride tris(4-methoxyphenyl)siloxide, magnesium chloride tris(2,2-dimethoxyphenyl)siloxide, magnesium chloride tris(3,3-dimethoxyphenyl)siloxide, magnesium chloride tris(2,3-dimethoxyphenyl)siloxide, magnesium chloride tris(2,4-dimethoxyphenyl)siloxide, magnesium chloride tris(3,4-dimethoxyphenyl)siloxide, magnesium chloride tris(2,4,6-trimethoxyphenyl)siloxide, magnesium chloride tris(2,3,4,5-tetramethoxyphenyl)siloxide, magnesium chloride tris(2,3,4,6-tetramethoxyphenyl)siloxide, magnesium chloride tris(2,3,5,6-tetramethoxyphenyl)siloxide, magnesium chloride tris(2,3,4,5,6-pentamethoxyphenyl)siloxide; magnesium chloride dimethylphenylsiloxide, magnesium chloride methyldiphenylsiloxide, magnesium chloride diethylphenylsiloxide, magnesium chloride ethyldiphenylsiloxide, magnesium chloride di(tert-butyl)phenylsiloxide, magnesium chloride tert-butyldiphenylsiloxide; magnesium chloride dimethyl (methylphenyl)siloxide, magnesium chloride methyldi(m-ethylphenyl)siloxide, magnesium chloride dimethyl(dimethylphenyl)siloxide, magnesium chloride methyldi(dimethylphenyl)siloxide, magnesium chloride dimethyl(trimethylphenyl)siloxide, magnesium chloride methyldi(trimethylphenyl)siloxide, magnesium chloride dimethyl(tetramethylphenyl)siloxide, magnesium chloride methyldi(tetramethylphenyl)siloxide, magnesium chloride dimethyl(pentamethylphenyl)siloxide, magnesium chloride methyldi(pentamethylphenyl)siloxide; magnesium chloride dimethyl(fluorophenyl)siloxide, magnesium chloride methyldi(fluorophenyl)siloxide, magnesium chloride dimethyl(difluorophenyl)siloxide, magnesium chloride methyldi(difluorophenyl)siloxide, magnesium chloride dimethyl(trifluorophenyl)siloxide, magnesium chloride methyldi(trifluorophenyl)siloxide, magnesium chloride dimethyl(tetrafluorophenyl)siloxide, magnesium chloride methyldi(tetrafluorophenyl)siloxide, magnesium chloride dimethyl(pentafluorophenyl)siloxide, magnesium chloride methyldi(pentafluorophenyl)siloxide; magnesium chloride dimethyl(methoxyphenyl)siloxide, magnesium chloride methyldi(methoxyphenyl)siloxide, magnesium chloride dimethyl(dimethoxyphenyl)siloxide, magnesium chloride methyldi(dimethoxyphenyl)siloxide, magnesium chloride dimethyl(trimethoxyphenyl)siloxide, magnesium chloride methyldi(trimethoxyphenyl)siloxide, magnesium chloride dimethyl(tetramethoxyphenyl)siloxide, magnesium chloride methyldi(tetramethoxyphenyl)siloxide, magnesium chloride dimethyl(pentamethoxyphenyl)siloxide, magnesium chloride methyldi(pentamethoxyphenyl)siloxide; magnesium chloride dimethyl(trifluoromethylphenyl)siloxide, magnesium chloride methyldi(trifluoromethylphenyl)siloxide, magnesium chloride dimethyl(di(trifluoromethyl)phenyl)siloxide, magnesium chloride methyldi(di(trifluoromethyl)phenyl)siloxide, magnesium chloride dimethyl(tri(trifluoromethyl)phenyl)siloxide, magnesium chloride methyldi(tri(trifluoromethyl)phenyl)siloxide, magnesium chloride dimethyl(tetra(trifluoromethyl)phenyl)siloxide, magnesium chloride methyldi(tetra(trifluoromethyl)phenyl)siloxide, magnesium chloride dimethyl(penta(trifluoromethyl)phenyl)siloxide, magnesium chloride methyldi(penta(trifluoromethyl)phenyl)siloxide, magnesium chloride di(tert-butyl)(trifluoromethylphenyl)siloxide, magnesium chloride methyldi(trifluoromethylphenyl)siloxide, magnesium chloride dimethyl(di(trifluoromethyl)phenyl)siloxide, magnesium chloride methyldi(di(trifluoromethyl)phenyl)siloxide, magnesium chloride dimethyl(tri(trifluoromethyl)phenyl)siloxide, magnesium chloride methyldi(tri(trifluoromethyl)phenyl)siloxide, magnesium chloride dimethyl(tetra(trifluoromethyl)phenyl)siloxide, magnesium chloride methyldi(tetra(trifluoromethyl)phenyl)siloxide, magnesium chloride dimethyl(penta(trifluoromethyl)phenyl)siloxide, magnesium chloride methyldi(penta(trifluoromethyl)phenyl)siloxide; diphenylsilanedioxy bis(magnesium chloride), di(methylphenyl)silanedioxy bis(magnesium chloride), di(dimethylphenyl)silanedioxy bis(magnesium chloride), di(trimethylphenyl)silanedioxy bis(magnesium chloride), di(tetramethylphenyl)silanedioxy bis(magnesium chloride), di(pentamethylphenyl)silanedioxy bis(magnesium chloride); di(fluorophenyl)silanedioxy bis(magnesium chloride), di(difluorophenyl)silanedioxy bis(magnesium chloride), di(trifluorophenyl)silanedioxy bis(magnesium chloride), di(tetrafluorophenyl)silanedioxy bis(magnesium chloride), di(pentafluorophenyl)silanedioxy bis(magnesium chloride); di(methoxyphenyl)silanedioxy bis(magnesium chloride), di(dimethoxyphenyl)silanedioxy bis(magnesium chloride), di(trimethoxyphenyl)silanedioxy bis(magnesium chloride), di(tetramethoxyphenyl)silanedioxy bis(magnesium chloride), di(pentamethoxyphenyl)silanedioxy bis(magnesium chloride); di(trifluoromethylphenyl)silanedioxy bis(magnesium chloride), di(di(trifluoromethyl)phenyl)silanedioxy bis(magnesium chloride), di(tri(trifluoromethyl)phenyl)silanedioxy bis(magnesium chloride), di(tetra(trifluoromethyl)phenyl)silanedioxy bis(magnesium chloride), di(penta(trifluoromethyl)phenyl)silanedioxy bis(magnesium chloride) or the like.

The compound represented by the general formula (I') is preferably the magnesium chloride compounds, and among them, magnesium chloride triphenylsiloxide, magnesium chloride tris(2-methylphenyl)siloxide, magnesium chloride tris(3-methylphenyl)siloxide, magnesium chloride tris(4-methylphenyl)siloxide, magnesium chloride tris(2-fluorophenyl)siloxide, magnesium chloride tris(3-fluorophenyl)siloxide, magnesium chloride tris(4-fluorophenyl)siloxide, magnesium chloride tris(2-methoxyphenyl)siloxide, magnesium chloride tris(3-methoxyphenyl)siloxide, magnesium chloride tris(4-methoxyphenyl)siloxide, magnesium chloride dimethylphenylsiloxide, diphenylsilanedioxy bis(magnesium chloride) and the like, are preferable.

The compound represented by the general formula (I') may be a coordinated compound, and may be, for example, a coordinated compound formed with the solvent relating to the present invention. For example, when the compound represented by the general formula (I') is coordinated with THF, it is estimated to form a coordinated compound of the following dimer.

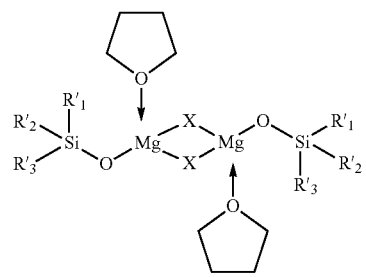

(wherein X, $R'_1$, $R'_2$ and $R'_3$ are the same as described above.)

[Production Method for the Compound Represented by the General Formula (I')]

The compound represented by the general formula (I') can be obtained, for example, by reacting a silanol compound represented by the following general formula (II') and the Grignard reagent, in a suitable solvent.

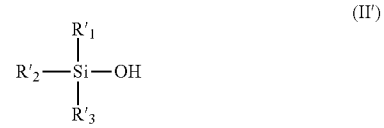

(wherein $R'_1$ to $R'_3$ are the same as described above.)

Specific examples of the compound represented by the general formula (II') include those corresponding to specific examples of the compound represented by the general formula (I'), and preferable examples also include those corresponding to preferable examples of the compound represented by the general formula (I').

As the compound represented by the general formula (II'), a commercial product may be used, or the compound produced by a method known per se may be used. The method known per se may be carried out by producing a compound represented by the following general formula (III') according to a method described, for example, in Paul D. Price et al., Dalton Tarnsactions, (2), 271-282, 2008, and then subjecting the compound to an oxidation reaction known per se.

(III')

(wherein R'$_1$ to R'$_3$ are the same as described above.)

Specific examples of the compound represented by the general formula (III') include those corresponding to specific examples of the compound represented by the general formula (I'), and preferable examples also include those corresponding to preferable examples of the compound represented by the general formula (I').

The Grignard reagent includes, for example, a compound represented by RMgX (R represents an alkyl group having 1 to 6 carbon atoms, which has a substituent, or a phenyl group which has a substituent, and X is the same as described above).

The alkyl group having 1 to 6 carbon atoms in R includes the same group as the alkyl group having 1 to 6 carbon atoms in R$_2$ and R$_3$. The substituent of the alkyl group and the phenyl group in R includes, for example, a halogeno group, an alkyl group, a halogenoalkyl group, an alkoxy group or the like, and the specific examples include the same examples as explained in a paragraph of the substituent of the aryl group in R$_1$.

Use amount of the Grignard reagent in a reaction of the silanol compound represented by the general formula (II') and the Grignard reagent is usually 0.5 to 2 mol, and preferably 0.5 to 1 mol, relative to 1 mol of the compound represented by the general formula (II').

Reaction temperature of the silanol compound represented by the general formula (II') and the Grignard reagent is usually −78 to 80° C., and reaction time is usually 5 seconds to 5 hours. In addition, the reaction is preferably carried out in inert gas atmosphere, such as argon, nitrogen or the like, and more preferably in argon atmosphere. A solvent to be used here may be any solvent, if at least one of the silanol compound represented by the general formula (II') or the Grignard reagent is soluble, and the solvent dissolving both compounds (reagents) is preferable. It specifically includes, for example, the same solvent as the solvent relating to the present invention, among them, an ether-type solvent, such as diethyl ether, diglyme, triglyme, tetraglyme, tetrahydrofuran, 2-methyltetrahydrofuran, diisopropyl ether, 1,2-dimethoxyethane, diethylene glycol dimethyl ether, triethylene glycol dimethyl ether, cyclopentyl methyl ether, t-butyl methyl ether, 1,4-dioxane or the like, and preferably tetrahydrofuran. It should be noted that a resulting reaction product may be washed with a solvent, such as diisopropyl ether or the like, after concentration and drying, as needed.

The compound represented by the general formula (I') is produced specifically, for example, as follows.

That is, the silanol compound represented by the general formula (II') is dissolved in a solvent, such as tetrahydrofuran or the like, in argon gas atmosphere. Still more, a tetrahydrofuran solution or the like, dissolved with 0.1 to 2 mol of phenyl magnesium chloride, relative to 1 mol of the silanol compound, is dropped, and is subjected to a reaction for 5 seconds to 5 hours. An operation to obtain a solid, such as by concentration and drying of a reaction solution, is carried out, as needed, and a resulting solid is washed with a solvent, such as diisopropyl ether or the like, and dried to produce the compound represented by the general formula (I').

Explanation on the present invention is given further specifically below, with reference to Examples and Comparative Examples, and the present invention should not be limited to these Examples.

EXAMPLES

Example 1: Preparation of an Electrolytic Solution 1

(1) Synthesis of a Magnesium Salt

Under argon gas atmosphere, benzophenone (7.29 g, 40 mmol) (Wako Pure Chemical Industries, Ltd.) was dissolved in tetrahydrofuran (THF) (20 mL) (Wako Pure Chemical Industries, Ltd.), and a THF solution of phenylmagnesium chloride (PhMgCl) (20 mL, 40 mmol) (Tokyo Chemical Industry Co., Ltd., 2 M) was added dropwise to the solution. After stirring for 4 hours, crystal was filtered off and dried to obtain magnesium chloride triphenylmethoxide (Ph$_3$COMgCl).

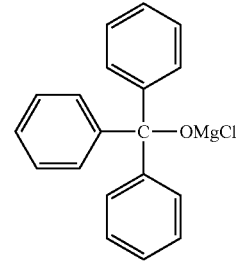

(2) Preparation of the Electrolytic Solution

Under argon gas atmosphere, magnesium chloride triphenylmethoxide (Ph$_3$COMgCl) (1.60 g, 5 mmol) was added to THF (20 mL). The mixture was heated to 50° C., and then aluminum chloride (AlCl$_3$) (0.67 g, 5 mmol) was added to the mixture. After maintaining the resulting mixture at 50° C. for 5 minutes, it was cooled and filtrated to obtain the electrolytic solution 1, "a solution of magnesium chloride triphenylmethoxide-aluminum chloride/THF".

Example 2: Preparation of an Electrolytic Solution 2

Under argon gas atmosphere, magnesium chloride triphenylmethoxide (Ph$_3$COMgCl) (1.60 g, 5 mmol), obtained in (1) of Example 1, was added to triglyme (20 mL). The mixture was heated to 50° C., and then aluminum chloride (AlCl$_3$) (0.17 g, 1.25 mmol) was added to the mixture. After maintaining the resulting mixture at 50° C. for 5 minutes, it was cooled and filtrated to obtain the electrolytic solution 2, "a solution of magnesium chloride triphenylmethoxide-aluminum chloride/triglyme".

Example 3: Preparation of an Electrolytic Solution 3

Under argon gas atmosphere, magnesium chloride triphenylmethoxide ($Ph_3COMgCl$) (1.60 g, 5 mmol), obtained in (1) of Example 1, was added to THF (20 mL). The mixture was heated to 35° C., and then dimethylaluminum chloride ($Me_2AlCl$) (0.48 g, 5 mmol) (concentrated from a hexane solution, purchased from Kanto Chemical Co., Inc.) was added dropwise to the mixture. After maintaining the resulting mixture at 50° C. for 5 minutes, it was cooled to obtain the electrolytic solution 3, "a solution of magnesium chloride triphenylmethoxide-dimethylaluminum chloride/THF".

Example 4: Preparation of an Electrolytic Solution 4

(1) Synthesis of a Magnesium Salt

Under argon gas atmosphere, into a THF solution of phenylmagnesium chloride (PhMgCl) (10 mL, 20 mmol) (Tokyo Chemical Industry Co., Ltd., 2 M), THF (30 mL) (Wako Pure Chemical Industries, Ltd.) was added, and then acetone (1.28 g, 22 mmol) (Wako Pure Chemical Industries, Ltd.) was added dropwise to the diluted solution. After stirring the solution for 2 hours, crystal was filtered off and dried to obtain magnesium chloride dimethylphenylmethoxide ($Me_2PhCOMgCl$).

(2) Preparation of the Electrolytic Solution

Under argon gas atmosphere, into magnesium chloride dimethylphenylmethoxide ($Me_2PhCOMgCl$) (0.97 g, 5 mmol), THF was mixed. The mixture was heated to 50° C., and then aluminum chloride ($AlCl_3$) (0.17 g, 1.25 mmol) was added to the mixture. After maintaining the resulting mixture at 50° C. for 5 minutes, it was cooled to obtain the electrolytic solution 4, "a solution of magnesium chloride dimethylphenylmethoxide-aluminum chloride/THF".

Example 5: Preparation of an Electrolytic Solution 5

Under argon gas atmosphere, benzophenone (7.29 g, 40 mmol) (Wako Pure Chemical Industries, Ltd.) was dissolved in THF (20 mL) (Wako Pure Chemical Industries, Ltd.), and then a THF solution of allylmagnesium chloride (($C_3H_5$)MgCl) (40 mL, 40 mmol) (Tokyo Chemical Industry Co., Ltd., 1 M) was added dropwise, and the solution was stirred for 4 hours. Aluminum chloride ($AlCl_3$) (0.17 g, 2 mmol) was added relative to the solution (12 mL, 8 mmol) at room temperature, and the resulting mixture was stirred for 1 hour to obtain the electrolytic solution 5, "a solution of magnesium chloride 1,1-diphenyl-1-(2-propenyl)methoxide-aluminum chloride/THF".

Example 6: Preparation of an Electrolytic Solution 6

Under argon gas atmosphere, 4,4-difluorobenzophenone (4.36 g, 20 mmol) (by Wako Pure Chemical Industries, Ltd.) was dissolved in tetrahydrofuran (THF) (15 mL) (Wako Pure Chemical Industries, Ltd.), and then a THF solution of phenylmagnesium chloride (PhMgCl) (10 mL, 20 mmol) (Tokyo Chemical Industry Co., Ltd., 2 M) was added dropwise, and the solution was stirred for 4 hours. After heating the resulting solution (6.8 m, 5 mmol) to 40° C., aluminum chloride ($AlCl_3$) (0.67 g, 5 mmol) was added to the solution and the resulting mixture was cooled to obtain the electrolytic solution 6, "a solution of magnesium chloride 1,1-di(4-fluorophenyl)-1-phenylmethoxide-aluminum chloride/THF".

Comparative Example 1: Preparation of a Comparative Electrolytic Solution 1

Under argon gas atmosphere, a THF solution of ethyl magnesium chloride (EtMgCl) (10 mL, 20 mmol) (Tokyo Chemical Industry Co., Ltd., 2 M) and THF (10 mL) (Wako Pure Chemical Industries, Ltd.) were combined, and then tert-butanol (1.48 g, 20 mmol) (Wako Pure Chemical Industries, Ltd.) was added dropwise to the diluted solution. Then, aluminum chloride (0.44 g, 3.3 mmol) (Wako Pure Chemical Industries, Ltd.) was added to the solution and the resulting mixture was stirred to obtain the comparative electrolytic solution 1, "a solution of (tert-BuOMgCl)$_6$—$AlCl_3$/THF".

Comparative Example 2: Preparation of a Comparative Electrolytic Solution 2

Under argon gas atmosphere, magnesium chloride (0.5 g, 5.3 mmol) (Wako Pure Chemical Industries, Ltd.) was dissolved in THF (21 mL) (Wako Pure Chemical Industries, Ltd.), and dimethylaluminum chloride ($Me_2AlCl$) (0.97 g, 10.5 mmol) (concentrated from a THF solution, purchased from Kanto Chemical Co., Inc.) was added dropwise, and then tetrabutylammonium chloride ($Bu_4NCl$) (1.46 g, 5.3 mmol) (Tokyo Chemical Industry Co., Ltd.) was added. The resulting mixture was stirred at 60° C. for 2 days, and cooled to obtain the comparative electrolytic solution 2, "a solution of $MgCl_2$-$Me_2AlCl$—$Bu_4NCl$/THF".

Example 7/Comparative Example 3: Cyclic Voltammetry (CV) Measurement of Various Electrolytic Solutions Cyclic voltammetry (CV) measurement for the electrolytic solutions 1 to 6 (Example 7) was carried out. In addition, CV measurement for the comparative electrolytic solutions 1 and 2 (Comparative Example 3) was carried out similarly.

CV measurement was carried out specifically as follows. That is, using a 3-electrode beaker cell, a platinum electrode (diameter: 3 mm; BAS Co. Ltd.), an Mg rod (diameter: 1.6 mm; The Nilaco Corp.), and an Mg rod (diameter: 1.6 mm; The Nilaco Corp.) were used as a working electrode, a counter electrode and a reference electrode, respectively. Into the beaker cell, 2 mL of the electrolytic solution was added to carry out the measurement at room temperature (25° C.), with a sweep rate of 5 mV/s, and within a range of −1.5 V to 3.5 V. An electrochemical measurement system (BioLogic Co., Ltd.) was used for this measurement.

Results of oxidation decomposition potential (after 10 cycles) of each electrolytic solution are shown in the following Table 1.

In addition, result of the electrolytic solution 1 after 10 cycles is shown in FIG. 1, and results of the electrolytic solution 2 after 10 cycles and 40 cycles, are shown in FIG. 2 and FIG. 3, respectively. Results of the comparative electrolytic solutions 1 and 2, after 10 cycles, are shown in FIGS. 4 and 5. It should be noted that the horizontal axis in these Figures represents potential of the working electrode, based on potential of the reference electrode, and the vertical axis (mA/cm²) represents current density obtained by dividing current value observed at each potential with surface area of the working electrode.

TABLE 1

| Electrolytic Solution | Magnesium salt | Solvent | Lewis acid | Oxidation decomposition potential |
|---|---|---|---|---|
| Electrolytic Solution 1 | Ph$_3$COMgCl | THF | AlCl$_3$ | +3.4 V |
| Electrolytic Solution 2 | Ph$_3$COMgCl | Triglyme | AlCl$_3$ | +3.2 V |
| Electrolytic Solution 3 | Ph$_3$COMgCl | THF | Me$_2$AlCl | +2.8 V |
| Electrolytic Solution 4 | Me$_2$PhCOMgCl | THF | AlCl$_3$ | +3.1 V |
| Electrolytic Solution 5 | (C$_3$H$_5$)Ph$_2$COMgCl | THF | AlCl$_3$ | +3.4 V |
| Electrolytic Solution 6 | (C$_6$H$_4$F)$_2$PhCOMgCl | THF | AlCl$_3$ | +2.8 V |
| Comparative Electrolytic Solution 1 | t-BuOMgCl | THF | AlCl$_3$ | +2.4 V |
| Comparative Electrolytic Solution 2 | MgCl$_2$ | THF | Me$_2$AlCl | +2.8 V |

From the results of Table 1, it has been revealed that the electrolytic solution of the present invention indicates oxidation decomposition potential of +2.8 V to +3.4 V, and can be used in equivalent or higher voltage as compared with a conventional method. Still more, from the results of FIG. 3, it has been revealed that the electrolytic solution 2 can be used stably without deterioration, even by repeating dissolution and deposition of magnesium 40 times.

On the other hand, the comparative electrolytic solution 2, "a solution of (t-BuOMgCl)$_6$—AlCl$_3$/THF", is an electrolytic solution described in J. Mater. Chem. A, 2014, 2, 581-584 (NON-PATENT LITERATURE 3). As a result of carrying out CV measurement using the electrolytic solution, it has been observed that oxidation decomposition potential thereof is +2.4 V, nearly as described in the LITERATURE.

Experimental Example 1: Observation of Copper Plate Surface Using a Scanning Electron Microscope (SEM)

It has been observed whether current in cyclic voltammetry (CV) measurement of the electrolytic solution 1 is the result associated with dissolution and deposition of Mg, using SEM (Hitachi High-Technologies Corp.).

Specifically, using a 3-electrode beaker cell, a copper plate (thickness: 0.1 mm; The Nilaco Corp.), an Mg rod (diameter: 1.6 mm; The Nilaco Corp.), and an Mg rod (diameter: 1.6 mm; produced by The Nilako Corp.) were used as a working electrode, a counter electrode and a reference electrode, respectively. Into the beaker cell, 2 mL of the electrolytic solution of Example 1 was added to deposit magnesium on the copper plate at room temperature (25° C.), under a current value of 0.1 mA for 5 hours. An electrochemical measurement system (BioLogic Co., Ltd) was used in the experiment.

As a result of observation of the copper plate surface after the deposition, deposition of magnesium has been observed by using the SEM. In addition, elemental analysis of magnesium, aluminum, copper, chlorine, carbon or oxygen was carried out using EDS (energy dispersive X-ray analysis), and it has also been observed that the deposited element was magnesium.

Example 8: Preparation of an Electrolytic Solution 7

Under argon gas atmosphere, triphenylsilanol (11.1 g, 40 mmol) (Tokyo Chemical Industry Co., Ltd.) was dissolved in tetrahydrofuran (THF) (20 mL) (Wako Pure Chemical Industries, Ltd.), and then a THF solution of phenylmagnesium chloride (PhMgCl) (20 mL, 40 mmol) (Tokyo Chemical Industry Co., Ltd., 2 M) was added dropwise to the solution, and the solution was stirred for 1 hour. After that, powder generated by concentration and drying of the solution, was washed with diisopropyl ether (70 mL) (Wako Pure Chemical Industries, Ltd.). The powder was filtered off and dried to obtain magnesium chloride triphenylsiloxide (Ph$_3$SiOMgCl).

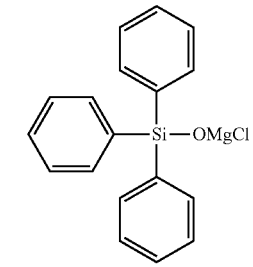

Measurement result of $^1$H-NMR is shown below.
$^1$H-NMR (400 MHz, CDCl$_3$) δ (ppm): 7.25-7.80 (m, 15H)
(2) Preparation of the Electrolytic Solution Under argon gas atmosphere, into magnesium chloride triphenylsiloxide (Ph$_3$SiOMgCl) (3.35 g, 10 mmol) was added to THF (40 mL) (Wako Pure Chemical Industries, Ltd.) was mixed. The mixture was heated to 50° C., and then aluminum chloride (AlCl$_3$) (1.33 g, 10 mmol) (Wako Pure Chemical Industries, Ltd.) was added to the mixture. After maintaining the resulting mixture at 50° C. for 10 minutes, it was cooled and filtrated after 1 week to obtain the electrolytic solution 7, "a solution of magnesium chloride triphenylsiloxide-aluminum chloride/THF".

Example 9: Preparation of an Electrolytic Solution 8

Under argon gas atmosphere, into magnesium chloride triphenylsiloxide (Ph$_3$SiOMgCl) (0.84 g, 2.5 mmol), obtained in Example 8 (1), THF (10 mL) (Wako Pure Chemical Industries, Ltd.) was mixed, and then a solution of boron trichloride (0.5 mL, 0.5 mmol) (BCl$_3$) (Wako Pure Chemical Industries, Ltd., 1 M solution in CH$_2$Cl$_2$) was added dropwise to the solution at room temperature. The resulting mixture was maintained at 50° C. for 10 minutes, and then it was concentrated, and tetrahydrofuran (THF) (10 mL) (Wako Pure Chemical Industries, Ltd.) was added. The resulting solution (8 mL, 2 mmol) was heated to 50° C., and then aluminum chloride (AlCl$_3$) (0.21 g, 1.6 mmol) (Wako Pure Chemical Industries, Ltd.) was added to the solution. After maintaining the resulting mixture at 50° C. for 10 minutes, it was cooled to obtain the electrolytic solution 8, "a solution of magnesium chloride triphenylsiloxide-aluminum chloride/THF".

Example 10: Preparation of an Electrolytic Solution 9

Under argon gas atmosphere, into magnesium chloride triphenylsiloxide (Ph₃SiOMgCl) (0.84 g, 2.5 mmol), obtained in Example 8 (1), triglyme (10 mL) (Wako Pure Chemical Industries, Ltd.) was mixed. The mixture was heated to 50° C., and then aluminum chloride (AlCl₃) (0.33 g, 2.5 mmol) (Wako Pure Chemical Industries, Ltd.) was added to the mixture. After maintaining the resulting mixture at 50° C. for 10 minutes, it was cooled and filtrated after 1 week to obtain the electrolytic solution 9, "a solution of magnesium chloride triphenylsiloxide-aluminum chloride/triglyme".

Example 11: Preparation of an Electrolytic Solution 10

(1) Tris(4-methylphenyl)silanol

Under nitrogen atmosphere, a THF solution of 4-methylphenylmagnesium bromide (288 mL, 288 mmol) (Tokyo Chemical Industry Co., Ltd., 1.0 M) was added into a 1000 mL flask. After that, a solution of trichlorosilane (12.2 g, 90 mmol) (Tokyo Chemical Industry Co., Ltd.) dissolved in THF (302 mL) was added dropwise for 1 hour, while keeping temperature of the solution in the flask below 35° C. After adding dropwise, the reaction mixture was further stirred at room temperature for 2 hours and subject to a reaction. After completion of the reaction, hydrochloric acid solution (45 mL, 1.0 M) was dropped for neutralization, and then diisopropyl ether (450 mL) (Wako Pure Chemical Industries, Ltd.) was added to the reaction mixture, and a mixture was subjected to a liquid separation. Still more, an organic layer was washed with hydrochloric acid solution (45 mL, 1.0 M), and a mixture was subjected to a liquid separation. An organic layer was dried by magnesium sulfate (30 g) (Wako Pure Chemical Industries, Ltd.). After filtration of magnesium sulfate, a filtrate was concentrated under reduced pressure to obtain a crude product of tris(4-methylphenyl)silane. Still more, the crude product was dissolved in diisopropyl ether (50 mL) and ethanol (50 mL), and the solution was subjected crystallization by concentrating under reduced pressure. After filtration of a deposited white solid, the solid was washed with ethanol (60 mL). The resulting solid was dried under reduced pressure to obtain tris(4-methylphenyl)silane (20.44 g, 67.6 mmol, yield: 75%, white solid).

¹H-NMR (400 MHz, CDCl₃) 2.36 (s, 9H, Me), 5.41 (s, 1H, SiH), 7.18 (d, 6H, J=8.2 Hz, Ar), 7.46 (d, 6H, J=8.2 Hz, Ar)

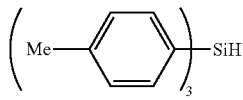

Next, under nitrogen atmosphere, the resulting tris(4-methylphenyl)silane (6.05 g, 20 mmol) and THF (375 mL) were added into the 1000 mL flask. Still more, potassium permanganate (3.32 g, 21 mmol) (Wako Pure Chemical Industries, Ltd.) and ion exchanged water (3.8 mL) were added to the solution. The mixture was stirred and subjected to a reaction at 60° C. for 13 hours, while applying ultrasonic wave to the flask, using an ultrasonic washing machine (US-2, AS ONE Corp.). After completion of the reaction, the reaction mixture was passed through silica gel (60 g) (C-200, Wako Pure Chemical Industries, Ltd.) to filtrate a byproduct, manganese oxide. The filtrate was concentrated under reduced pressure to obtain a crude product of tris(4-methylphenyl)silanol. The crude product was dissolved in dichloromethane (30 mL) (Wako Pure Chemical Industries, Ltd.) and n-hexane (60 mL) (Wako Pure Chemical Industries, Ltd.), and the solution was subjected crystallization by concentration under reduced pressure. After filtration of a deposited white solid, the solid was washed with n-hexane (10 mL). The resulting solid was dried under reduced pressure to obtain tris(4-methylphenyl)silanol (3.1 g, 9.58 mmol, yield: 48%, white solid).

¹H-NMR (400 MHz, C₆D₆) (ppm): 1.89 (s, 1H, SiOH), 2.10 (s, 9H, Me), 7.06 (d, 6H, J=8.2 Hz, Ar), 7.68 (d, 6H, J=8.2 Hz, Ar)

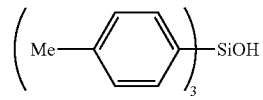

(2) Synthesis of a Magnesium Salt

Under argon gas atmosphere, the resulting tris(4-methylphenyl)silanol (2.55 g, 8 mmol) was dissolved in tetrahydrofuran (THF) (12 mL) (Wako Pure Chemical Industries, Ltd.), and then a THF solution of phenylmagnesium chloride (PhMgCl) (3.8 mL, 7.6 mmol) (Tokyo Chemical Industry Co., Ltd., 2 M) was added dropwise, and the solution was stirred for 1 hour. After that, powder generated by concentration and drying of the solution, was washed with diisopropyl ether (30 mL) (Wako Pure Chemical Industries, Ltd.). The powder was filtered off and dried to obtain magnesium chloride tris(4-methylphenyl)siloxide ((4-Me-C₆H₄)₃SiOMgCl).

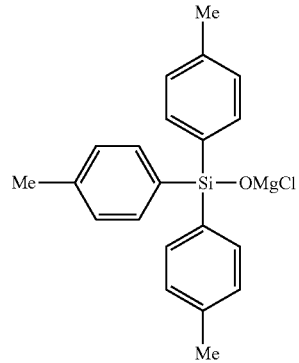

Measurement result of ¹H-NMR is shown below.

¹H-NMR (400 MHz, CDCl₃) δ (ppm): 2.33 (s, 9H), 7.14-7.17 (d, 6H, J=7.0 Hz), 7.58-7.61 (d, 6H, J=7.0 Hz)

(3) Preparation of the Electrolytic Solution

Under argon gas atmosphere, into magnesium chloride tris(4-methylphenyl)siloxide ((4-Me-C₆H₄)₃SiOMgCl) (0.94 g, 2.5 mmol), THF (10 mL) (Wako Pure Chemical Industries, Ltd.) was mixed. The mixture was heated to 50° C., and then aluminum chloride (AlCl₃) (0.33 g, 2.5 mmol) (Wako Pure Chemical Industries, Ltd.) was added to the mixture. After maintaining the resulting mixture at 50° C. for 10 minutes, it was cooled to obtain the electrolytic solution 10, "a solution of magnesium chloride tris(4-methylphenyl)siloxide-aluminum chloride/THF".

Example 12: Preparation of an Electrolytic Solution 11

(1) Synthesis of tris(4-fluoro)silanol

Under nitrogen atmosphere, a THF solution of 4-fluorophenylmagnesium bromide (288 mL, 288 mmol) (Tokyo Chemical Industry Co., Ltd., 1.0 M) was added into a 1000 mL flask. After that, a solution of trichlorosilane (12.2 g, 90 mmol) (Tokyo Chemical Industry Co., Ltd.) dissolved in THF (302 mL) was added dropwise for 1 hour, while keeping temperature of the solution in the flask below 35° C. After adding dropwise, the reaction mixture was further stirred at room temperature for 2 hours and subjected to a reaction. After completion of the reaction, hydrochloric acid solution (45 mL, 1.0 M) was dropped for neutralization, and then diisopropyl ether (450 mL) was added to the reaction mixture, and the reaction mixture, and a mixture was subjected to a liquid separation. Still more, an organic layer was washed with hydrochloric acid solution (45 mL, 1.0 M), and a mixture was subjected to a liquid separation. A resulting organic layer was dried by magnesium sulfate (30 g) (Wako Pure Chemical Industries, Ltd.). After filtration of magnesium sulfate, a filtrate was concentrated under reduced pressure to obtain a crude product of tris(4-fluorophenyl) silane. Still more, n-pentane (30 mL) (Wako Pure Chemical Industries, Ltd.) was added to the crude product to eliminate only oil out colored component by using a dropping pipet. The remained solution was concentrated under reduced pressure, and then a deposited solid was filtrated and washed with ethanol (30 mL). The resulting white solid was dried under reduced pressure to obtain tris(4-fluorophenyl)silane (22.68 g, 72.1 mmol, yield: 80%, white solid).

$^1$H-NMR (400 MHz, CDCl$_3$) 5.44 (s, 1H, SiH), 7.05-7.11 (m, 6H, Ar), 7.47-7.52 (m, 6H, Ar)

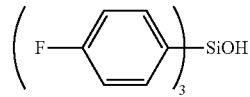

Next, under nitrogen atmosphere, the resulting tris(4-fluorophenyl)silane (6.29 g, 20 mmol) and THF (375 mL) were added into the 1000 mL flask. Still more, potassium permanganate (3.32 g, 21 mmol) (Wako Pure Chemical Industries, Ltd.) and ion exchanged water (3.8 mL) were added to the solution. The mixture was stirred and subjected to a reaction for 4 hours by maintaining the mixture below room temperature, while applying ultrasonic wave to the flask, using an ultrasonic washing machine (US-2, AS ONE Corp.). After completion of the reaction, the reaction mixture was passed through silica gel (60 g) (C-200, Wako Pure Chemical Industries, Ltd.) to filtrate a byproduct, manganese oxide. The filtrate was concentrated under reduced pressure to obtain a crude product of tris(4-fluorophenyl)silanol. After purification by silica gel column chromatography (eluent: ethyl acetate/n-hexane=1/9; ethyl acetate and n-hexane are both purchased from Wako Pure Chemical Industries, Ltd.), it was dried under reduced pressure to obtain tris(4-fluorophenyl)silanol (2.55 g, 7.72 mmol, yield: 39%, white solid).

$^1$H-NMR (400 MHz, CDCl$_3$) δ: 2.50 (s, 1H, SiOH), 7.07-7.14 (m, 6H, Ar), 7.54-7.60 (m, 6H, Ar)

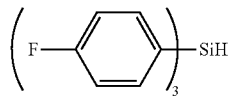

(2) Synthesis of a Magnesium Salt

Under argon gas atmosphere, the resulting tris(4-fluorophenyl)silanol (2.15 g, 6.5 mmol) was dissolved in tetrahydrofuran (THF) (19.5 mL) (Wako Pure Chemical Industries, Ltd.), and then a THF solution of phenylmagnesium chloride (PhMgCl) (3.1 mL, 6.2 mmol) (Tokyo Chemical Industry Co., Ltd., 2 M) was added dropwise at −78° C., and the solution was stirred for 1 hour. To an oil component generated by concentration and drying of the solution, hexane (50 mL) (Wako Pure Chemical Industries, Ltd.) and diisopropyl ether (30 mL) (Wako Pure Chemical Industries, Ltd.) were added to generate powder. The powder was filtered off and dried to obtain magnesium chloride tris(4-fluorophenyl)siloxide ((4-F—C$_6$H$_4$)$_3$SiOMgCl).

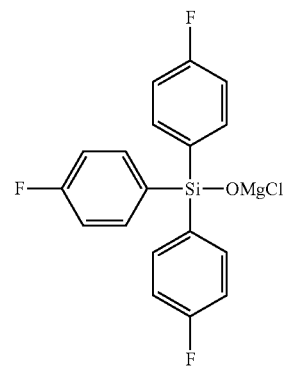

Measurement result of $^1$H-NMR is shown below.

$^1$H-NMR (400 MHz, CDCl$_3$) δ (ppm): 7.06-7.11 (t, 6H, J=8.8 Hz), 7.64-7.68 (t, 6H, J=7.0 Hz)

(3) Preparation of the Electrolytic Solution

Under argon gas atmosphere, into magnesium chloride tris(4-fluorophenyl)siloxide ((4-F—C$_6$H$_4$)$_3$SiOMgCl) (0.86 g, 2.2 mmol), THF (8.8 mL) (Wako Pure Chemical Industries, Ltd.) was mixed. The mixture was heated to 50° C., and then aluminum chloride (AlCl$_3$) (0.29 g, 2.2 mmol) (Wako Pure Chemical Industries, Ltd.) was added to the mixture. After maintaining the resulting mixture at 50° C. for 10 minutes, it was cooled to obtain the electrolytic solution 11, "a solution of magnesium chloride tris(4-fluorophenyl)siloxide-aluminum chloride/THF".

Example 13: Preparation of an Electrolytic Solution 12

(1) Synthesis of tris(3,5-dimethoxyphenyl)silanol

Magnesium flake (6.36 g, 0.262 mmol) (Wako Pure Chemical Industries, Ltd.) and iodine (10 mg) (Wako Pure Chemical Industries, Ltd.) were added into a 2000 mL flask, and dried under reduced pressure for 1 hour. Still more, under nitrogen atmosphere, tetrahydrofuran (222 mL) (Wako Pure Chemical Industries, Ltd.) was added to the flask. Next, a solution of 1-bromo-3,5-dimethoxybenzene (52.1 g, 0.240 mmol) (Tokyo Chemical Industry Co., Ltd.)

dissolved in tetrahydrofuran (274 mL) (Wako Pure Chemical Industries, Ltd.) was added dropwise for 1.5 hour. After adding dropwise, the reaction mixture was stirred at room temperature for 1 hour. Then, a solution of trichlorosilane (10.2 g, 0.075 mmol) (Tokyo Chemical Industry Co., Ltd.) dissolved in tetrahydrofuran (252 mL) (Wako Pure Chemical Industries, Ltd.) was added dropwise for 1 hour, while keeping temperature inside the flask below 35° C. After adding dropwise, the mixture was stirred at room temperature for 1 hour. After completion of the reaction, hydrochloric acid solution (45 mL, 1.0 M) (Wako Pure Chemical Industries, Ltd.) was dropped for neutralization, and then diisopropyl ether (450 mL) (Wako Pure Chemical Industries, Ltd.) was added to the reaction mixture, and the reaction mixture was subjected to a liquid separation. Still more, an organic layer was washed with hydrochloric acid solution (45 mL, 1.0 M) (Wako Pure Chemical Industries, Ltd.), and a mixture was subjected to a liquid separation. An organic layer was dried by magnesium sulfate (30 g) (Wako Pure Chemical Industries, Ltd.). After filtration of magnesium sulfate, a filtrate was concentrated under reduced pressure to obtain a crude product of tris(3,5-dimethoxyphenyl)silane. The resulting crude product was dissolved in diisopropyl ether (50 mL) (Wako Pure Chemical Industries, Ltd.) and ethanol (30 mL) (Wako Pure Chemical Industries, Ltd.), and the solution was subjected to crystallization by concentration under reduced pressure. After filtration of a deposited white solid, the solid was washed with ethanol (30 mL). The resulting solid was dried under reduced pressure to obtain tris(3,5-dimethoxyphenyl)silane (28.7 g, 65.0 mmol, yield: 87%, white solid).

$^1$H-NMR (400 MHz, CDCl$_3$) δ (ppm): 3.75 (s, 18H, OMe), 5.34 (s, 1H, SiH), 6.50 (t, 3H, J=2.4 Hz, Ar), 6.71 (d, 6H, J=2.4 Hz, Ar)

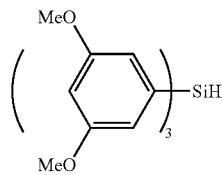

Next, under nitrogen atmosphere, the resulting tris(3,5-dimethoxyphenyl)silane (8.81 g, 20 mmol) and THF (375 mL) were added into a 1000 mL flask. Still more, potassium permanganate (3.32 g, 21 mmol) (Wako Pure Chemical Industries, Ltd.) and ion exchanged water (3.8 mL) were added to the solution. The mixture was stirred and subjected to a reaction for 1 hour by maintaining the mixture below room temperature, while applying ultrasonic wave to the flask, using an ultrasonic washing machine (US-2, AS ONE Corp.). After completion of the reaction, the reaction mixture was passed through silica gel (60 g) (C-200, Wako Pure Chemical Industries, Ltd.) to filtrate a byproduct, manganese oxide. The filtrate was concentrated under reduced pressure to obtain a crude product of tris(3,5-dimethoxyphenyl)silanol. The resulting crude product was dissolved in dichloromethane (20 mL) (Wako Pure Chemical Industries, Ltd.) and n-hexane (30 mL) (Wako Pure Chemical Industries, Ltd.), and the solution was subjected to crystallization by concentration under reduced pressure. After filtration of a deposited white solid, the solid was washed with n-hexane (30 mL). The resulting solid was dried under reduced pressure to obtain tris(3,5-dimethoxyphenyl)silanol (7.68 g, 16.8 mmol, yield: 84%, white solid).

$^1$H-NMR (400 MHz, CDCl$_3$) δ (ppm): 2.46 (s, 1H, SiOH), 3.75 (s, 18H, OMe), 6.52 (t, 3H, J=2.4 Hz, Ar), 6.76 (d, 6H, J=2.4 Hz, Ar)

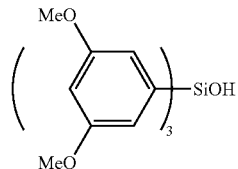

(2) Synthesis of a Magnesium Salt

Under argon gas atmosphere, the resulting tris(3,5-dimethoxyphenyl)silanol (3.65 g, 8 mmol) was dissolved in THF (30 mL), and then a THF solution of phenylmagnesium chloride (PhMgCl) (3.8 mL, 7.6 mmol) (Tokyo Chemical Industry Co., Ltd., 2 M) was added dropwise, and the solution was stirred for 1 hour. After that, powder generated by concentration and drying of the solution, was washed with diisopropyl ether (36.5 mL) (Wako Pure Chemical Industries, Ltd.). The powder was filtered off and dried to obtain magnesium chloride tris(3,5-dimethoxyphenyl)siloxide ((3,5-(MeO)$_2$—C$_6$H$_3$)$_3$SiOMgCl).

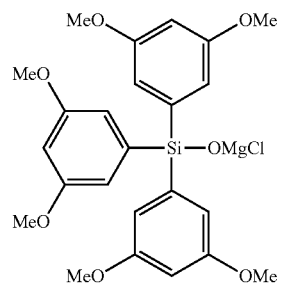

Measurement result of $^1$H-NMR is shown below.

$^1$H-NMR (400 MHz, CDCl$_3$) δ (ppm): 3.75 (s, 18H), 6.44-6.48 (t, 3H, J=2.4 Hz), 6.80-6.91 (d, 6H, J=2.4 Hz)

(3) Preparation of the Electrolytic Solution

Under argon gas atmosphere, into magnesium chloride tris(3,5-dimethoxyphenyl)siloxide ((3,5-(MeO)$_2$—C$_6$H$_3$)$_3$SiOMgCl) (1.29 g, 2.5 mmol), THF (10 mL) was mixed. The mixture was heated to 50° C., and then aluminum chloride (AlCl$_3$) (0.33 g, 2.5 mmol) (Wako Pure Chemical Industries, Ltd.) was added to the mixture. After maintaining the resulting mixture at 50° C. for 10 minutes, it was cooled to obtain the electrolytic solution 12, "a solution of magnesium chloride tris(3,5-dimethoxyphenyl)siloxide-aluminum chloride/THF".

Example 14: Preparation of an Electrolytic Solution 13

(1) Synthesis of a Magnesium Salt

Under argon gas atmosphere, dimethylphenylsilanol (4.57 g, 30 mmol) (Wako Pure Chemical Industries, Ltd.) was dissolved in tetrahydrofuran (THF) (15 mL) (Wako Pure Chemical Industries, Ltd.), and then a THF solution of phenylmagnesium chloride (PhMgCl) (15 mL, 30 mmol) (Tokyo Chemical Industry Co., Ltd., 2 M) was added dropwise, and the solution was stirred for 1 hour. To an oil component generated by concentration and drying of the solution, hexane (30 mL) (Wako Pure Chemical Industries, Ltd.) and tert-butyl methyl ether (85 mL) (Wako Pure Chemical Industries, Ltd.) were added to generate powder. The powder was filtered off and dried to obtain magnesium chloride dimethylphenylsiloxide (Me₂PhSiOMgCl).

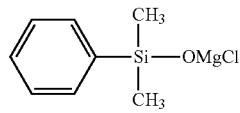

Measurement result of ¹H-NMR is shown below.
¹H-NMR (400 MHz, CDCl₃) δ (ppm): 0.20-0.60 (m, 6H), 7.20-7.40 (m, 3H), 7.50-7.70 (m, 2H)

(2) Preparation of the Electrolytic Solution

Under argon gas atmosphere, into magnesium chloride dimethylphenylsiloxide (Me₂PhSiOMgCl) (1.06 g, 5 mmol), THF (20 mL) (Wako Pure Chemical Industries, Ltd.) was mixed. The mixture was heated to 50° C., and then aluminum chloride (AlCl₃) (0.67 g, 5 mmol) (Wako Pure Chemical Industries, Ltd.) was added to the mixture. After maintaining the resulting mixture at 50° C. for 10 minutes, it was cooled to obtain the electrolytic solution 13, "a solution of magnesium chloride dimethylphenylsiloxide-aluminum chloride/THF".

Example 15: Preparation of an Electrolytic Solution 14

(1) Synthesis of a Magnesium Salt

Under argon gas atmosphere, diphenylsilanediol (8.65 g, 40 mmol) (Tokyo Chemical Industry Co., Ltd.) was dissolved in tetrahydrofuran (THF) (20 mL) (Wako Pure Chemical Industries, Ltd.), and then a THF solution of phenylmagnesium chloride (PhMgCl) (40 mL, 80 mmol) (Tokyo Chemical Industry Co., Ltd., 2 M) was added dropwise, and the solution was stirred for 1 hour. After that, powder generated by concentration and drying of the solution, was washed with diisopropyl ether (50 mL) (Wako Pure Chemical Industries, Ltd.). The powder was filtered off and dried to obtain diphenylsilanedioxy bis(magnesium chloride), (Ph₂Si(OMgCl)₂).

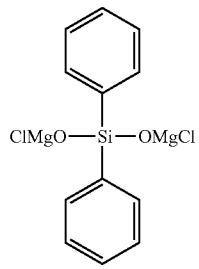

Measurement result of ¹H-NMR is shown below.
¹H-NMR (400 MHz, CDCl₃) δ (ppm): 6.90-8.00 (m, 10H)

(2) Preparation of the Electrolytic Solution

Under argon gas atmosphere, into diphenylsilanedioxy bis(magnesium chloride) (Ph₂Si(OMgCl)₂) (0.83 g, 2.5 mmol), THF (20 mL) (Wako Pure Chemical Industries, Ltd.) was mixed. The mixture was heated to 50° C., and then aluminum chloride (AlCl₃) (0.67 g, 5 mmol) (Wako Pure Chemical Industries, Ltd.) was added to the mixture. After maintaining the resulting mixture at 50° C. for 10 minutes, it was cooled to obtain the electrolytic solution 14, "a solution of diphenylsilanedioxy bis(magnesium chloride)-aluminum chloride/THF".

Comparative Example 4: Preparation of a Comparative Electrolytic Solution 3

Under argon gas atmosphere, trimethylsilanol (Me₃SiOH) (0.90 g, 10 mmol) (Sigma-Aldrich Co., LLC.) was added dropwise to a THF solution of ethylmagnesium chloride (EtMgCl) (5 mL, 10 mmol) (Tokyo Chemical Industry Co., Ltd., 2 M), and the solution was air-cooled. At room temperature, aluminum chloride (AlCl₃) (0.22 g, 1.67 mmol) (Wako Pure Chemical Industries, Ltd.) was added to the solution, and the solution was stirred for 1 hour to obtain the comparative electrolytic solution 3, "a solution of (Me₃SiOMgCl)₆—AlCl₃/THF".

Example 16: Preparation of an Electrolytic Solution 15

(1) Synthesis of a Magnesium Salt

Under argon gas atmosphere, triphenylsilanol (5.53 g, 20 mmol) (Tokyo Chemical Industry Co., Ltd.) was dissolved in tetrahydrofuran (THF) (20 mL) (Wako Pure Chemical Industries, Ltd.), and then a THF solution of phenylmagnesium bromide (PhMgBr) (10 mL, 10 mmol) (Tokyo Chemical Industry Co., Ltd., 1 M) was added dropwise, and subjected to a reaction for 1 hour. After that, to an oil component generated by concentration and drying of the solution, diisopropyl ether (40 mL) (Wako Pure Chemical Industries, Ltd.) was added to generate powder. The powder was filtered off and dried to obtain magnesium bromide triphenylsiloxide (Ph₃SiOMgBr).

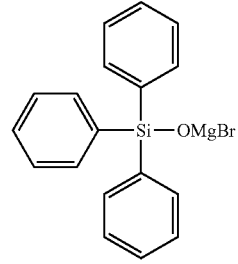

Measurement result of ¹H-NMR is shown below.
¹H-NMR (400 MHz, CDCl₃) δ (ppm): 6.95-7.90 (m, 15H)

(2) Preparation of the Electrolytic Solution

Under argon gas atmosphere, into magnesium bromide triphenylsiloxide (Ph₃SiOMgBr) (0.95 g), THF (10 mL) (Wako Pure Chemical Industries, Ltd.) was mixed. The mixture was heated to 50° C., and then aluminum chloride (AlCl₃) (0.33 g, 2.5 mmol) (Wako Pure Chemical Industries, Ltd.) was added to the mixture. After maintaining the resulting mixture at 50° C. for 10 minutes, it was cooled and filtrated to obtain the electrolytic solution 15, "a solution of magnesium bromide triphenylsiloxide-aluminum chloride/THF".

Example 17/Comparative Example 5: Cyclic Voltammetry (CV) Measurement of Various Electrolytic Solutions Cyclic voltammetry (CV) measurement for the electrolytic solutions 7 to 15 (Example 17) was carried out similarly as in Example 7. In addition, CV measurement for the comparative electrolytic solution 3 (Comparative Example 5) was carried out similarly as in Example 7.

Results of oxidation decomposition potential of each electrolytic solution are shown in the following Table 2.

In addition, result of the electrolytic solution 7 after 10 cycles is shown in FIG. 6, and result of the comparative electrolytic solution 3 after 10 cycles is shown in FIG. 7. It should be noted that the horizontal axis in these Figures represents potential of the working electrode, based on potential of the reference electrode, and the vertical axis (mA/cm$^2$) represents current density obtained by dividing current value observed at each potential with surface area of the working electrode.

TABLE 2

| Electrolytic Solution | Magnesium salt | Solvent | Lewis acid | Oxidation decomposition potential |
|---|---|---|---|---|
| Electrolytic Solution 7 | Ph$_3$SiOMgCl | THF | AlCl$_3$ | +3.2 V |
| Electrolytic Solution 8 | Ph$_3$SiOMgCl | THF | AlCl$_3$/BCl$_3$ | +3.0 V |
| Electrolytic Solution 9 | Ph$_3$SiOMgCl | Triglyme | AlCl$_3$ | +3.1 V |
| Electrolytic Solution 10 | (4-Me—C$_6$H$_4$)$_3$SiOMgCl | THF | AlCl$_3$ | +3.1 V |
| Electrolytic Solution 11 | (4-F—C$_6$H$_4$)$_3$SiOMgCl | THF | AlCl$_3$ | +3.0 V |
| Electrolytic Solution 12 | (3,5-(MeO)$_2$—C$_6$H$_3$)$_3$SiOMgCl | THF | AlCl$_3$ | +2.9 V |
| Electrolytic Solution 13 | Me$_2$PhSiOMgCl | THF | AlCl$_3$ | +3.1 V |
| Electrolytic Solution 14 | Ph$_2$Si(OMgCl)$_2$ | THF | AlCl$_3$ | +2.9 V |
| Electrolytic Solution 15 | Ph$_3$SiOMgBr | THF | AlCl$_3$ | +2.8 V |
| Comparative Electrolytic Solution 3 | Me$_3$SiOMgCl | THF | AlCl$_3$ | +2.5 V |

From the results of Table 2, it has been revealed that the electrolytic solution of the present invention using a silicon-type compound indicates oxidation decomposition potential of +2.8 V to +3.2 V, and exhibits higher value as compared with a conventional method, thus can be used in high voltage.

In addition, as for the electrolytic solution 7, it has also been observed to exhibit oxidation decomposition potential of +3.2 V, by carrying out CV measurement, using the electrolytic solution after storage for 1 month. Therefore, it has also been revealed that the electrolytic solution of the present invention is superior in storage stability.

The invention claimed is:

1. An electrolytic solution for a magnesium battery comprising a mixture of a compound represented by the following general formula (I), a Lewis acid and a solvent:

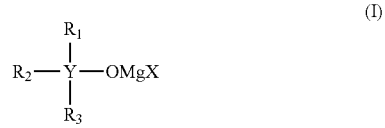

(I)

wherein Y represents a carbon atom or a silicon atom, X represents a chlorine atom or a bromine atom, R$_1$ represents an aryl group having 6 to 10 carbon atoms, which may have a halogeno group, an alkyl group, a halogenoalkyl group or an alkoxy group, as a substituent, R$_2$ and R$_3$ each independently represent a magnesium chloride oxy group (—OMgCl); a magnesium bromide oxy group (—OMgBr); an alkenyl group having 1 to 6 carbon atoms; an alkyl group having 1 to 6 carbon atoms, which may have a halogeno group or an alkoxy group, as a substituent; or an aryl group having 6 to 10 carbon atoms, which may have a halogeno group, an alkyl group, a halogenoalkyl group or an alkoxy group, as a substituent.

2. The electrolytic solution for a magnesium battery according to claim 1, wherein the Lewis acid contains beryllium, boron, aluminum, silicon, tin, titanium, chromium, iron, or cobalt, as an element.

3. The electrolytic solution for a magnesium battery according to claim 1, wherein the Lewis acid contains aluminum, as an element.

4. The electrolytic solution for a magnesium battery according to claim 1, wherein the Lewis acid is aluminum chloride.

5. The electrolytic solution for a magnesium battery according to claim 1, wherein R$_1$ in the compound is an aryl group having 6 to 10 carbon atoms, which may have a halogeno group, an alkyl group or an alkoxy group, as a substituent, R$_2$ and R$_3$ each independently represent a magnesium chloride oxy group (—OMgCl); an alkenyl group having 1 to 6 carbon atoms; an alkyl group having 1 to 6 carbon atoms; or an aryl group having 6 to 10 carbon atoms, which may have a halogeno group, an alkyl group or an alkoxy group, as a substituent.

6. The electrolytic solution for a magnesium battery according to claim 1, wherein R$_1$ in the compound is a phenyl group which may have a halogeno group, an alkyl group or an alkoxy group, as a substituent, R$_2$ and R$_3$ each independently represent —OMgCl; an alkenyl group having 1 to 6 carbon atoms; an alkyl group having 1 to 6 carbon atoms; or a phenyl group having an alkyl group as a substituent.

7. The electrolytic solution for a magnesium battery according to claim 1, wherein X in the compound is a chlorine atom.

8. The electrolytic solution for a magnesium battery according to claim 1, wherein the solvent is an ether-type solvent, a halogenated hydrocarbon-type solvent, a carbonate-type solvent or a nitrile-type solvent.

9. An electrochemical device comprising the electrolytic solution according to claim 1, a positive electrode and a negative electrode.

10. A compound represented by the following general formula (I'):

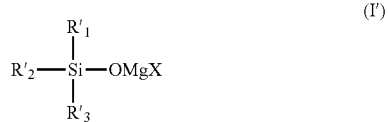

(I')

wherein X represents a chlorine atom, R'$_1$ represents an aryl group having 6 to 10 carbon atoms, which may have a halogeno group, an alkyl group, a halogenoalkyl group or an alkoxy group, as a substituent, R'$_2$ and R'$_3$ each independently represent a magnesium chloride oxy group (—OMgCl); a magnesium bromide oxy group (—OMgBr); an alkenyl group having 1 to 6 carbon atoms; an alkyl group having 1 to 6 carbon atoms, which may have a halogeno group or an alkoxy group; or an aryl group having 6 to 10 carbon atoms, which may have a halogeno group, an alkyl group, a halogenoalkyl group or an alkoxy group, as a substituent.

11. The compound according to claim 10, wherein R'$_2$ represents a magnesium chloride oxy group (—OMgCl); a magnesium bromide oxy group (—OMgBr); an alkenyl group having 1 to 6 carbon atoms; or an aryl group having 6 to 10 carbon atoms, which may have a halogeno group, an alkyl group, a halogenoalkyl group or an alkoxy group, as a substituent.

* * * * *